(12) United States Patent
Miraki et al.

(10) Patent No.: US 10,188,383 B2
(45) Date of Patent: Jan. 29, 2019

(54) SUTURE CLIP DEPLOYMENT DEVICES

(71) Applicant: Edwards Lifesciences Corporation, Irvine, CA (US)

(72) Inventors: Manouchehr A. Miraki, Laguna Hills, CA (US); Bryan A. Janish, Huntington Beach, CA (US); Kevin K. Dang, Garden Grove, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 372 days.

(21) Appl. No.: 14/757,938

(22) Filed: Dec. 23, 2015

(65) Prior Publication Data

US 2016/0183937 A1 Jun. 30, 2016

Related U.S. Application Data

(60) Provisional application No. 62/096,749, filed on Dec. 24, 2014.

(51) Int. Cl.
*A61B 17/04* (2006.01)
*A61B 17/29* (2006.01)

(52) U.S. Cl.
CPC ...... *A61B 17/0487* (2013.01); *A61B 17/0467* (2013.01); *A61B 17/0485* (2013.01);
(Continued)

(58) Field of Classification Search
CPC . A61B 17/0485; A61B 17/0487; A61B 17/08; A61B 17/083; A61B 17/10;
(Continued)

(56) References Cited

U.S. PATENT DOCUMENTS

| 1,358,477 A | 11/1920 | Stout |
|---|---|---|
| 2,264,679 A | 12/1941 | Ravel |

(Continued)

FOREIGN PATENT DOCUMENTS

| CA | 2141911 A1 | 8/1995 |
|---|---|---|
| CA | 2141913 A1 | 8/1995 |

(Continued)

OTHER PUBLICATIONS

European Search Report issued for Application No. 12858766.4, dated Sep. 16, 2015.
(Continued)

*Primary Examiner* — Ryan J Severson
(74) *Attorney, Agent, or Firm* — Klarquist Sparkman, LLC

(57) ABSTRACT

Disclosed herein are suture clip delivery devices that can be loaded with several flat, disk-shaped suture clips and can deploy the suture clips one after another onto respective sutures without reloading the device with additional suture clips. An exemplary device includes a handle portion with an actuation mechanism that is coupled to a shaft portion that holds and deploys the suture clips. The shaft portion includes a mandrel on which the suture clips are mounted and a retainer that restricts the suture clips from moving proximally when the actuation mechanism pulls the mandrel proximally, which causes a distal-most suture clip to slide off the mandrel and be deployed onto one or more suture. The mandrel and remaining suture clips can them move distally to prepare to deploy the next suture clip.

16 Claims, 18 Drawing Sheets

(52) U.S. Cl.
CPC ... *A61B 17/0469* (2013.01); *A61B 2017/0488* (2013.01); *A61B 2017/2913* (2013.01); *A61B 2017/2923* (2013.01)

(58) Field of Classification Search
CPC . A61B 17/105; A61B 17/122; A61B 17/1222; A61B 17/1227; A61B 17/128; A61B 17/1285; A61B 2017/0488; A61B 2017/049
See application file for complete search history.

(56) References Cited

U.S. PATENT DOCUMENTS

| | | | |
|---|---|---|---|
| 2,516,710 | A | 7/1950 | Mascolo |
| 2,715,486 | A | 8/1955 | Marcoff-Moghadam et al. |
| 2,890,519 | A | 6/1959 | Storz, Jr. |
| 2,981,990 | A | 5/1961 | Balderree, Jr. |
| 3,143,742 | A | 8/1964 | Cromie |
| 3,249,104 | A | 5/1966 | Hohnstein |
| 3,274,658 | A | 9/1966 | Pile |
| 3,452,742 | A | 7/1969 | Muller |
| 3,506,012 | A | 4/1970 | Brown |
| 3,509,882 | A | 5/1970 | Blake |
| 3,541,591 | A | 11/1970 | Hoegerman |
| 3,547,103 | A | 12/1970 | Cook |
| 3,570,497 | A | 3/1971 | Lemole |
| 3,608,095 | A | 9/1971 | Barry |
| 3,638,654 | A | 2/1972 | Akuba |
| RE27,391 | E | 6/1972 | Merser |
| 3,753,438 | A | 8/1973 | Wood et al. |
| 3,859,668 | A | 1/1975 | Anderson |
| 3,875,648 | A | 4/1975 | Bone |
| 3,898,999 | A | 8/1975 | Haller |
| 3,910,281 | A | 10/1975 | Kletschka et al. |
| 3,954,108 | A | 5/1976 | Davis |
| 3,954,109 | A | 5/1976 | Patel |
| 3,958,576 | A | 5/1976 | Komiya |
| 3,976,079 | A | 8/1976 | Samuels et al. |
| 3,988,810 | A | 11/1976 | Emery |
| 3,996,623 | A | 12/1976 | Kaster |
| 4,038,725 | A | 8/1977 | Keefe |
| 4,039,078 | A | 8/1977 | Bone |
| 4,103,690 | A | 8/1978 | Harris |
| 4,140,125 | A | 2/1979 | Smith |
| 4,170,990 | A | 10/1979 | Baumgart et al. |
| 4,192,315 | A | 3/1980 | Hilzinger et al. |
| 4,217,902 | A | 8/1980 | March |
| 4,324,248 | A | 4/1982 | Perlin |
| 4,345,601 | A | 8/1982 | Fukuda |
| 4,416,266 | A | 11/1983 | Baucom |
| 4,456,017 | A | 6/1984 | Miles |
| 4,485,816 | A | 12/1984 | Krumme |
| 4,522,207 | A | 6/1985 | Klieman et al. |
| 4,535,764 | A | 8/1985 | Ebert |
| 4,548,202 | A | 10/1985 | Duncan |
| 4,549,545 | A | 10/1985 | Levy |
| 4,570,304 | A | 2/1986 | Montreuil et al. |
| 4,586,502 | A | 5/1986 | Bedi et al. |
| 4,586,503 | A | 5/1986 | Kirsch et al. |
| 4,595,007 | A | 6/1986 | Mericle |
| 4,612,932 | A | 9/1986 | Caspar et al. |
| 4,637,380 | A | 1/1987 | Orejola |
| 4,665,906 | A | 5/1987 | Jervis |
| 4,683,895 | A | 8/1987 | Pohndorf |
| 4,705,040 | A | 11/1987 | Mueller et al. |
| 4,719,924 | A | 1/1988 | Crittenden et al. |
| 4,730,615 | A | 3/1988 | Sutherland et al. |
| 4,741,330 | A | 5/1988 | Hayhurst |
| 4,743,253 | A | 5/1988 | Magladry |
| 4,750,492 | A | 6/1988 | Jacobs |
| 4,809,695 | A | 3/1989 | Gwathmey et al. |
| 4,823,794 | A | 4/1989 | Pierce |
| 4,863,460 | A | 9/1989 | Magladry |
| 4,873,975 | A | 10/1989 | Walsh et al. |
| 4,896,668 | A | 1/1990 | Popoff et al. |
| 4,899,744 | A | 2/1990 | Fujitsuka et al. |
| 4,901,721 | A | 2/1990 | Hakki |
| 4,914,789 | A | 4/1990 | Pedersen |
| 4,924,866 | A | 5/1990 | Yoon |
| 4,926,860 | A | 5/1990 | Stice et al. |
| 4,929,240 | A | 5/1990 | Kirsch et al. |
| 4,932,955 | A | 6/1990 | Merz et al. |
| 4,950,283 | A | 8/1990 | Dzubow et al. |
| 4,950,285 | A | 8/1990 | Wilk |
| 4,955,913 | A | 9/1990 | Robinson |
| 4,976,715 | A | 12/1990 | Bays et al. |
| 4,983,176 | A | 1/1991 | Cushman et al. |
| 4,990,152 | A | 2/1991 | Yoon |
| 4,997,439 | A | 3/1991 | Chen |
| 5,002,550 | A | 3/1991 | Li |
| 5,002,562 | A | 3/1991 | Oberlander |
| 5,002,563 | A | 3/1991 | Pyka et al. |
| 5,026,379 | A | 6/1991 | Yoon |
| 5,047,047 | A | 9/1991 | Yoon |
| 5,053,047 | A | 10/1991 | Yoon |
| 5,070,805 | A | 12/1991 | Plante |
| 5,071,431 | A | 12/1991 | Sauter et al. |
| 5,074,874 | A | 12/1991 | Yoon et al. |
| 5,078,731 | A | 1/1992 | Hayhurst |
| 5,100,418 | A | 3/1992 | Yoon et al. |
| 5,116,840 | A | 5/1992 | Ganguly et al. |
| 5,123,913 | A | 6/1992 | Wilk et al. |
| RE34,021 | E | 8/1992 | Mueller et al. |
| 5,152,769 | A | 10/1992 | Baber |
| 5,154,189 | A | 10/1992 | Oberlander |
| 5,158,566 | A | 10/1992 | Pianetti |
| 5,163,954 | A | 11/1992 | Curcio et al. |
| 5,171,250 | A | 12/1992 | Yoon |
| 5,171,251 | A | 12/1992 | Bregen et al. |
| 5,171,252 | A | 12/1992 | Friedland |
| 5,174,087 | A | 12/1992 | Bruno |
| 5,196,022 | A | 3/1993 | Bilweis |
| 5,219,358 | A | 6/1993 | Bendel et al. |
| 5,222,976 | A | 6/1993 | Yoon |
| 5,231,735 | A | 8/1993 | Paxton |
| 5,234,449 | A | 8/1993 | Bruker et al. |
| 5,236,440 | A | 8/1993 | Hlavacek |
| 5,242,456 | A | 9/1993 | Nash et al. |
| 5,246,443 | A | 9/1993 | Mai |
| 5,258,011 | A | 11/1993 | Drews |
| 5,258,015 | A | 11/1993 | Li et al. |
| 5,269,783 | A | 12/1993 | Sander |
| 5,269,809 | A | 12/1993 | Hayhurst et al. |
| 5,282,832 | A | 2/1994 | Toso et al. |
| 5,290,289 | A | 3/1994 | Sanders et al. |
| 5,304,204 | A | 4/1994 | Bregen |
| 5,306,290 | A | 4/1994 | Martins et al. |
| 5,306,296 | A | 4/1994 | Wright et al. |
| 5,312,423 | A | 5/1994 | Rosenbluth et al. |
| 5,312,436 | A | 5/1994 | Coffey et al. |
| 5,330,442 | A | 7/1994 | Green et al. |
| 5,330,503 | A | 7/1994 | Yoon |
| 5,336,239 | A | 8/1994 | Gimpelson |
| 5,356,424 | A | 10/1994 | Buzerak et al. |
| 5,374,268 | A | 12/1994 | Sander |
| 5,381,588 | A | 1/1995 | Nelson |
| 5,383,904 | A | 1/1995 | Totakura et al. |
| 5,383,905 | A | 1/1995 | Golds et al. |
| 5,391,173 | A | 2/1995 | Wilk |
| 5,403,346 | A | 4/1995 | Loeser |
| 5,409,499 | A | 4/1995 | Yi |
| 5,437,680 | A | 8/1995 | Yoon |
| 5,437,685 | A | 8/1995 | Blasnik |
| 5,439,479 | A | 8/1995 | Shichman et al. |
| 5,445,167 | A | 8/1995 | Yoon et al. |
| 5,450,860 | A | 9/1995 | O'Connor |
| 5,452,733 | A | 9/1995 | Sterman et al. |
| 5,456,246 | A | 10/1995 | Schmieding et al. |
| 5,462,558 | A * | 10/1995 | Kolesa .............. A61B 17/0487 606/139 |
| 5,462,561 | A | 10/1995 | Voda |
| 5,474,557 | A | 12/1995 | Mai |
| 5,474,572 | A | 12/1995 | Hayhurst |
| 5,480,405 | A | 1/1996 | Yoon |

(56) References Cited

U.S. PATENT DOCUMENTS

| | | |
|---|---|---|
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,520,702 A | 5/1996 | Sauer et al. |
| 5,527,342 A | 6/1996 | Pietrzak et al. |
| 5,531,763 A | 7/1996 | Mastri et al. |
| 5,545,178 A | 8/1996 | Kensey et al. |
| 5,549,619 A | 8/1996 | Peters et al. |
| 5,562,685 A | 10/1996 | Mollenauer et al. |
| 5,569,274 A | 10/1996 | Rapacki et al. |
| 5,569,301 A | 10/1996 | Granger et al. |
| 5,573,543 A | 11/1996 | Akopov et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,626,590 A | 5/1997 | Wilk |
| 5,630,824 A | 5/1997 | Hart |
| 5,632,752 A | 5/1997 | Buelna |
| 5,632,753 A | 5/1997 | Loeser |
| 5,634,584 A | 6/1997 | Okorocha et al. |
| 5,643,289 A | 7/1997 | Sauer et al. |
| 5,643,295 A | 7/1997 | Yoon |
| 5,645,553 A | 7/1997 | Kolesa et al. |
| 5,645,568 A | 7/1997 | Chervitz et al. |
| 5,665,109 A | 9/1997 | Yoon |
| 5,669,917 A | 9/1997 | Sauer et al. |
| 5,669,935 A | 9/1997 | Rosenman et al. |
| 5,681,351 A | 10/1997 | Jamiolkowski et al. |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,725,556 A | 3/1998 | Moser et al. |
| 5,728,135 A | 3/1998 | Bregen et al. |
| 5,735,290 A | 4/1998 | Sterman et al. |
| 5,735,877 A | 4/1998 | Pagedas |
| 5,766,183 A | 6/1998 | Sauer |
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,833,696 A | 11/1998 | Whitfield et al. |
| 5,845,645 A | 12/1998 | Bonutti |
| 5,849,019 A | 12/1998 | Yoon |
| 5,852,851 A | 12/1998 | Cooper |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,393 A | 4/1999 | Pagedas |
| 5,895,394 A | 4/1999 | Kienzle et al. |
| 5,919,207 A | 7/1999 | Taheri |
| 5,948,001 A | 9/1999 | Larsen |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,231,592 B1 | 5/2001 | Bonutti et al. |
| 6,241,765 B1 | 6/2001 | Griffin et al. |
| 6,254,615 B1 | 7/2001 | Bolduc et al. |
| 6,306,141 B1 | 10/2001 | Jervis |
| 6,346,112 B2 | 2/2002 | Adams |
| 6,368,334 B1 | 4/2002 | Sauer |
| 6,432,123 B2 | 8/2002 | Schwartz et al. |
| 6,475,230 B1 | 11/2002 | Bonutti et al. |
| 6,514,265 B2 | 2/2003 | Ho et al. |
| 6,533,796 B1 | 3/2003 | Sauer et al. |
| 6,537,290 B2 | 3/2003 | Adams et al. |
| 6,551,332 B1 | 4/2003 | Nguyen et al. |
| 6,589,279 B1 | 7/2003 | Anderson et al. |
| 6,607,541 B1 | 8/2003 | Gardiner et al. |
| 6,613,059 B2 | 9/2003 | Schaller et al. |
| 6,626,930 B1 | 9/2003 | Allen et al. |
| 6,641,592 B1 | 11/2003 | Sauer et al. |
| 6,641,593 B1 | 11/2003 | Schaller et al. |
| 6,682,540 B1 | 1/2004 | Sancoff et al. |
| 6,719,767 B1 | 4/2004 | Kimblad |
| 6,746,457 B2 | 6/2004 | Dana et al. |
| 6,749,622 B2 | 6/2004 | McGuckin, Jr. et al. |
| 6,776,784 B2 | 8/2004 | Ginn |
| 6,860,890 B2 | 3/2005 | Bachman et al. |
| 6,896,686 B2 | 5/2005 | Weber |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,960,221 B2 | 11/2005 | Ho et al. |
| 7,011,669 B2 | 3/2006 | Kimblad |
| 7,083,628 B2 | 8/2006 | Bachman |
| 7,094,244 B2 | 8/2006 | Schreck |
| 7,112,207 B2 | 9/2006 | Allen et al. |
| 7,220,266 B2 | 5/2007 | Gambale |
| 7,235,086 B2 | 6/2007 | Sauer et al. |
| 7,264,625 B1 | 9/2007 | Buncke |
| 7,381,210 B2 | 6/2008 | Zarbatany et al. |
| 7,435,251 B2 * | 10/2008 | Green ............... A61B 17/0487 606/142 |
| 7,628,797 B2 | 12/2009 | Tieu et al. |
| 7,677,525 B2 | 3/2010 | Sanchez et al. |
| 7,731,727 B2 | 6/2010 | Sauer |
| 7,833,237 B2 | 11/2010 | Sauer |
| 7,842,051 B2 | 11/2010 | Dana et al. |
| 7,862,548 B2 | 1/2011 | Javer et al. |
| 7,862,584 B2 | 1/2011 | Lyons et al. |
| 7,875,056 B2 | 1/2011 | Jervis et al. |
| 7,959,674 B2 | 6/2011 | Shu et al. |
| 7,981,139 B2 | 7/2011 | Martin et al. |
| 8,021,421 B2 | 9/2011 | Fogarty et al. |
| 8,100,923 B2 | 1/2012 | Paraschac et al. |
| 8,105,355 B2 | 1/2012 | Page et al. |
| 8,252,005 B2 | 8/2012 | Findlay, III et al. |
| 8,398,657 B2 | 3/2013 | Sauer |
| 8,398,680 B2 | 3/2013 | Sauer et al. |
| 8,425,555 B2 | 4/2013 | Page et al. |
| 8,465,505 B2 | 6/2013 | Murillo et al. |
| 8,480,686 B2 | 7/2013 | Bakos et al. |
| 8,523,880 B2 * | 9/2013 | Kissel ............... A61B 17/0487 606/139 |
| 8,753,373 B2 | 6/2014 | Chau et al. |

(56) References Cited

U.S. PATENT DOCUMENTS

| | | | |
|---|---|---|---|
| 9,017,347 B2 | 4/2015 | Oba et al. | |
| 9,414,837 B2* | 8/2016 | Oba | A61B 17/0487 |
| 9,498,202 B2* | 11/2016 | Jafari | A61B 17/0401 |
| 9,549,730 B2* | 1/2017 | Oba | A61B 17/0487 |
| 9,592,048 B2* | 3/2017 | Moehle | A61B 17/0487 |
| 2001/0025181 A1 | 9/2001 | Freedlan | |
| 2002/0029060 A1 | 3/2002 | Hogendijk | |
| 2003/0009196 A1 | 1/2003 | Peterson | |
| 2003/0109922 A1 | 6/2003 | Peterson et al. | |
| 2003/0195563 A1 | 10/2003 | Foerster | |
| 2003/0233105 A1 | 12/2003 | Gayton | |
| 2004/0181238 A1 | 9/2004 | Zarbatany et al. | |
| 2004/0204724 A1 | 10/2004 | Kissel et al. | |
| 2004/0249414 A1 | 12/2004 | Kissel et al. | |
| 2005/0251206 A1 | 11/2005 | Maahs et al. | |
| 2005/0251209 A1 | 11/2005 | Saadat et al. | |
| 2006/0047314 A1 | 3/2006 | Green | |
| 2006/0079913 A1 | 4/2006 | Whitfield et al. | |
| 2006/0089571 A1 | 4/2006 | Gertner | |
| 2006/0184203 A1 | 8/2006 | Martin et al. | |
| 2006/0265010 A1 | 11/2006 | Paraschac et al. | |
| 2006/0276871 A1 | 12/2006 | Lamson et al. | |
| 2006/0282119 A1 | 12/2006 | Perchik | |
| 2007/0005079 A1 | 1/2007 | Zarbatany et al. | |
| 2007/0005081 A1 | 1/2007 | Findlay et al. | |
| 2007/0043384 A1 | 2/2007 | Ortiz et al. | |
| 2007/0049952 A1 | 3/2007 | Weiss | |
| 2007/0049970 A1 | 3/2007 | Belef et al. | |
| 2007/0088391 A1 | 4/2007 | McAlexander et al. | |
| 2007/0179530 A1 | 8/2007 | Tieu et al. | |
| 2007/0255296 A1 | 11/2007 | Sauer | |
| 2007/0270907 A1 | 11/2007 | Stokes et al. | |
| 2008/0154286 A1 | 6/2008 | Abbott et al. | |
| 2008/0255591 A1 | 10/2008 | Harada et al. | |
| 2008/0281356 A1 | 11/2008 | Chau et al. | |
| 2009/0143821 A1 | 6/2009 | Stupak | |
| 2009/0272783 A1 | 11/2009 | Crainich et al. | |
| 2009/0281377 A1 | 11/2009 | Newell et al. | |
| 2009/0281568 A1 | 11/2009 | Cendan et al. | |
| 2010/0001038 A1 | 1/2010 | Levin et al. | |
| 2010/0076462 A1 | 3/2010 | Bakos et al. | |
| 2010/0324597 A1 | 12/2010 | Shikhman | |
| 2010/0324598 A1 | 12/2010 | Anderson | |
| 2011/0087241 A1 | 4/2011 | Nguyen | |
| 2011/0087242 A1 | 4/2011 | Pribanic et al. | |
| 2011/0224485 A1 | 9/2011 | Boulnois et al. | |
| 2011/0224714 A1 | 9/2011 | Gertner | |
| 2011/0283514 A1 | 11/2011 | Fogarty et al. | |
| 2012/0080495 A1 | 4/2012 | Holcomb et al. | |
| 2012/0089182 A1 | 4/2012 | Page et al. | |
| 2012/0101526 A1 | 4/2012 | Bennett | |
| 2012/0102526 A1 | 4/2012 | Lejeune | |
| 2013/0053884 A1 | 2/2013 | Roorda | |
| 2013/0110164 A1 | 5/2013 | Milazzo et al. | |
| 2013/0158600 A1 | 6/2013 | Conklin et al. | |
| 2013/0267998 A1 | 10/2013 | Vijay et al. | |
| 2013/0282028 A1 | 10/2013 | Conklin et al. | |
| 2014/0031864 A1 | 1/2014 | Jafari et al. | |
| 2014/0303652 A1* | 10/2014 | Oba | A61B 17/0487 606/144 |
| 2015/0018879 A1* | 1/2015 | Moehle | A61B 17/0487 606/232 |
| 2015/0142021 A1 | 5/2015 | Smith et al. | |

FOREIGN PATENT DOCUMENTS

| | | |
|---|---|---|
| CN | 2558335 Y | 7/2003 |
| DE | 69512446 T2 | 5/2000 |
| DE | 69612447 T2 | 7/2001 |
| EP | 0669101 A1 | 8/1995 |
| EP | 0669103 A1 | 8/1995 |
| EP | 1484023 A1 | 12/2004 |
| GB | 2337934 A | 12/1999 |
| WO | 01049207 A2 | 7/2001 |
| WO | 0166001 A2 | 9/2001 |
| WO | 2004112841 A2 | 12/2004 |
| WO | 2013096313 A1 | 6/2013 |
| WO | 2014011794 A1 | 1/2014 |
| WO | 2015074040 A1 | 5/2015 |

OTHER PUBLICATIONS

International Search Report for PCT/US2014/046423, dated Oct. 20, 2014.
EP Supplementary Search Report for EP12858766, completed Sep. 7, 2015.
CN Office Action for App No. 2012800690769, dated Mar. 23, 2015.
European Supplementary Search Report dated Feb. 9, 2016 for EP13817447.
Int'l. Search Report dated Sep. 1, 2015 for PCT/US2015/032271.
Int'l. Search Report for PCT/US2012/070354, dated Apr. 4, 2013.
Int'l. Search Report from PCT Application No. PCT/US2013/049958, dated Oct. 8, 2013.
Int'l. Search Report for PCT/US2014/046423, dated Oct. 20, 2014.
Int'l. Search Report for PCT/US14/66122 dated Feb. 11, 2015.
LSI Solutions T-Knot Device 2, LSI Solutions, Inc., 2009-2011, http://www.lsisolutions.com/tkoutsideofcannula.
LSI Solutions T-Knot Device, LSI Solutions, Inc., 2009-2011, http://www.lsisolutions.com/tkatscrubtable.
TK Quick Load, LSI Solutions, http://www.lsisolutions.com/tkquickload.
Int'l. Search Report for PCT/US2015/032271, dated Sep. 1, 2015.
International Search Reportof PCT/US15/65033 dated Feb. 18, 2016.
Int'l. Search Report for PCT/US2015/000255, dated May 4, 2016.
Office Action and Search Report issued in CN2013800370375, dated Mar. 28, 2016.
Int'l. Search Report for PCT/US2016/022495, dated Jun. 1, 2016.

* cited by examiner

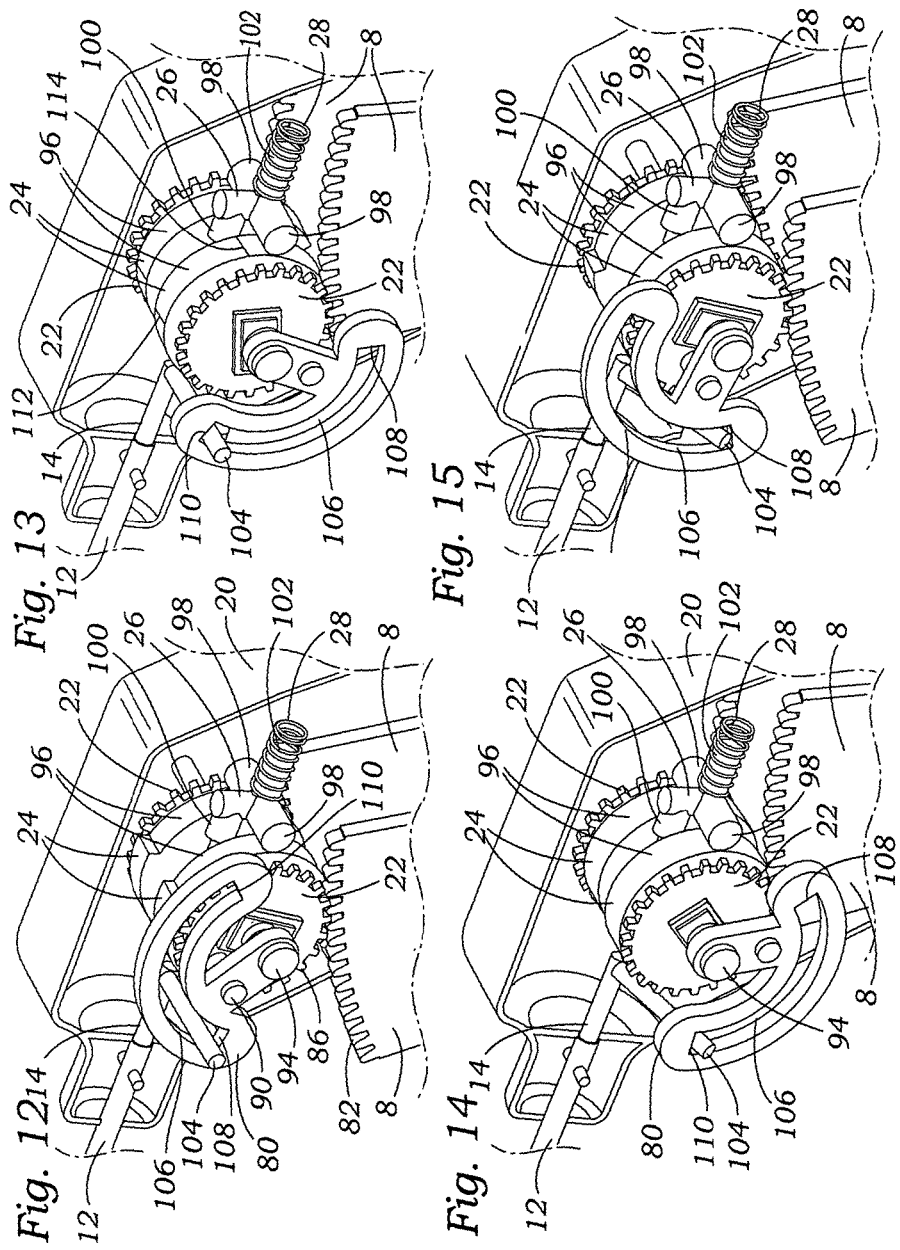

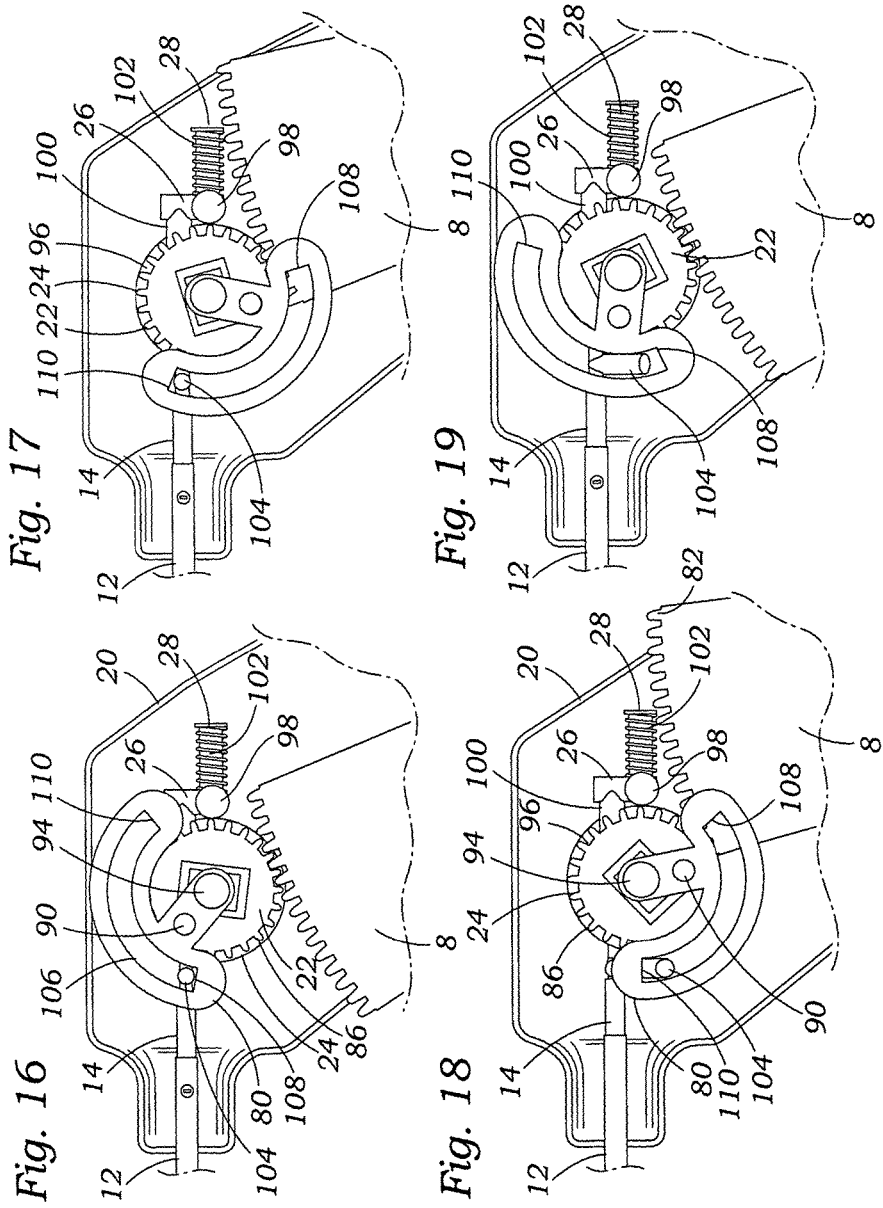

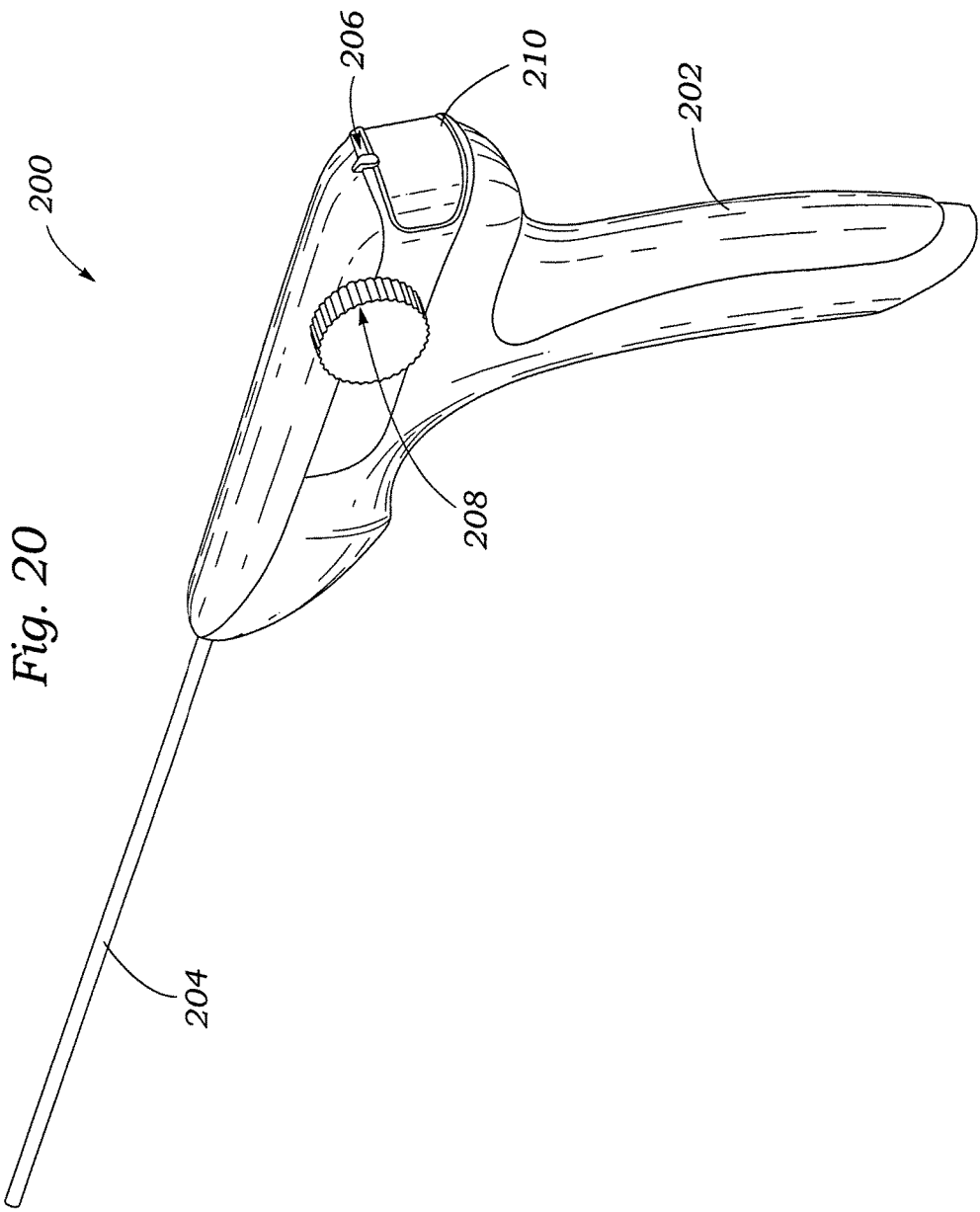

SUTURE CLIP DEPLOYMENT DEVICES

CROSS-REFERENCE TO RELATED APPLICATIONS

This application claims the benefit of U.S. Provisional Patent Application No. 62/096,749 filed Dec. 24, 2014, which is incorporated by reference herein in its entirety.

This application is also related to U.S. patent application Ser. No. 14/868,741, filed Sep. 29, 2015; U.S. patent application Ser. No. 14/543,240, filed Nov. 17, 2014; U.S. Pat. No. 9,017,347, issued on Apr. 28, 2015; U.S. patent application Ser. No. 13/938,071, filed Jul. 9, 2013; U.S. patent application Ser. No. 14/307,694, filed Jun. 18, 2014; U.S. patent application Ser. No. 14/329,797, filed Jul. 11, 2014; U.S. patent application Ser. No. 14/965,323, filed Dec. 10, 2015; and U.S. patent application Ser. No. 14/658,575, filed Mar. 16, 2015; all which are incorporated by reference herein in their entireties.

FIELD

This disclosure relates to suture clips and devices and methods for securing sutures using suture clips.

BACKGROUND

Sutures are used for a variety of surgical purposes, such as approximation of tissue and ligation of tissue. When placing sutures, the strand of suture material to be used typically has a needle affixed to one end which is passed (looped) through the tissue to be approximated or ligated, forming a stitch. The stitch is then tensioned appropriately, and the two free ends of the suture loop, the needle end and the non-needle end, are knotted to retain the desired tension in the stitch. Forming knots in suture during open surgery is a simple matter, though time-consuming, but forming knots in sutures during endoscopic surgery can require two surgeons to cooperate in a multi-step process which is performed with multiple instruments to pass the needle and suture back and forth to tie the suture knot.

Suture locking devices that eliminate the need to tie knots in order to speed up surgical procedures are known. Suture retainers or locks are used in place of suture knots to prevent passage of a suture end into and through tissue and to maintain the tension applied to the suture material during a suturing procedure.

When using a method that employs a clip to secure sutures, the clip can be delivered by advancing the clip along the suture lines to the area of interest, and then engaging the clip to the sutures such that the clip secures the sutures in place. With the clip thus secured, the excess sutures can be cut and removed from the patient. However, deployment of several suture clips during a procedure can be very time consuming, difficult to accomplish without error, and prone to inconsistent tensioning from one clip to the next. In light of the foregoing, there is presently a need for improved systems for securing sutures with suture clips.

SUMMARY

Disclosed herein are improved suture clip delivery devices that can be loaded with and deliver several suture clips to respective sutures in succession without reloading the device with additional suture clips. Disclosed devices and methods can be useful for securing heart valve repair devices or valve replacement prostheses in or near the heart, for example. The devices and methods can also be used for various other types of surgical procedures. The devices and methods disclosed herein can eliminate the need for suture knots, thus reducing surgical time and exposure. Further, the disclosed devices and methods can improve the ease of implantation because the clinician need not tie knots in the limited space in and around the target anatomy.

An exemplary disk-shaped suture clip disclosed herein includes an annular outer body, one or more resiliently deformable flaps that project radially inwardly from the annular outer body and define a suture engagement aperture for frictionally engaging one or more sutures passing therethrough, and one or more tabs projecting radially outwardly from the annular outer body. The suture clip is generally disk-shaped with the outer body, flaps, and tabs being substantially coplanar when the suture clip in its natural configuration. The one or more tabs project radially outwardly from the outer perimeter of the annular outer body. In some embodiments, the clip includes two or more radially projecting tabs spaced about the outer perimeter of the annular outer body. The suture clip has a resiliently deformed configuration when mounted on the delivery device, wherein the one or more resiliently deformable flaps are deflected out of a plane defined by the annular outer body and the one or more tabs, such that the suture engagement aperture enlarges sufficiently to receive a mandrel of the device.

Some embodiments of suture clip delivery devices described herein comprise a proximal handle portion including an actuation mechanism and a shaft portion including a mandrel loaded with plural suture clips. The mandrel has an inner lumen for receiving sutures, a proximal end portion coupled to the actuation mechanism, and a distal end portion having a distal opening in communication with the inner lumen. The suture clips are mounted annularly around the distal end portion of the mandrel. The suture clips are generally disk shaped and have a diameter oriented in the radial dimension of the shaft portion and a thickness oriented in the axial dimension of the shaft portion, wherein the thickness is substantially smaller than the diameter.

The actuation mechanism causes the mandrel to move proximally relative to the suture clips, such that a distal-most one of the suture clips slides off of a distal end of the mandrel and onto one or more sutures extending into the distal opening of the mandrel. After the distal-most one of the suture clips is deployed onto one or more sutures, the actuation mechanism causes the mandrel and a remaining portion of the suture clips to move distally relative to the handle portion such that a distal-most one of the remaining portion of the suture clips is ready to be successively deployed.

The shaft portion can also include a retainer positioned at least partially around the mandrel and coupled to the actuation mechanism independently of the mandrel. The retainer is configured to restrict the suture clips from moving proximally relative to the handle portion when the mandrel moves proximally relative to the handle portion. The actuation mechanism causes the retainer to rotate relative to the mandrel and the suture clips. This rotation can cause cutting of the one or more sutures and/or can free the suture clips to move distally along with the mandrel relative to the handle portion.

The retainer can include at least one axially extending slot that includes a plurality of circumferentially extending notches. The radially extending tabs on the suture clips can project into the axially extending slot in the retainer and can be positioned in respective ones of the circumferentially extending notches. The retainer can have a first rotational position wherein the suture clip tabs are positioned in the notches, such that axial motion of the suture clips relative to the retainer is restricted, and the retainer can have a second rotational position wherein the suture clip tabs are not positioned in the notches and the suture clips are allowed to move axially relative to the retainer. In the second position, the clips can move distally along with the mandrel to reset the device after each suture clip deployment.

In some embodiments, the shaft portion includes an electrical heating element positioned at a distal end of the mandrel and the heating element is configured to cut a suture after a suture clip is deployed onto the suture. The heating element can be coupled to a switch in the handle portion that is activated for a short time when the actuator is depressed.

A further understanding of the features and advantages of the disclosed technology will become apparent from a consideration of the following detailed description.

BRIEF DESCRIPTION OF THE DRAWINGS

FIGS. 12-15 are perspective views of an actuation mechanism within the handle portion shown in FIG. 11, illustrating the motion of the actuation mechanism in four sequential positions.

FIGS. 16-19 are side views that correspond with the sequential positions shown in FIGS. 12-15.

FIG. 20 shows another embodiment of suture clip deployment device.

DETAILED DESCRIPTION

Described herein are devices and methods for securing sutures with suture clips. FIGS. 1-5 and 7-19 illustrate an exemplary suture clip deployment device 2. The device 2 can be loaded with one or more suture clips, such as the exemplary disk-shaped suture clip 18 shown in FIG. 6, and can be used to deploy loaded suture clips in succession onto one or more sutures, such as during implantation of a prosthetic device within the heart. While any of the disclosed suture clips can be used to secure a single suture, or can be used to secure plural sutures or suture segments at the same time, this description proceeds with reference to non-limiting examples wherein each suture clip is deployed onto two sutures segments for ease of description only.

Figure 1:
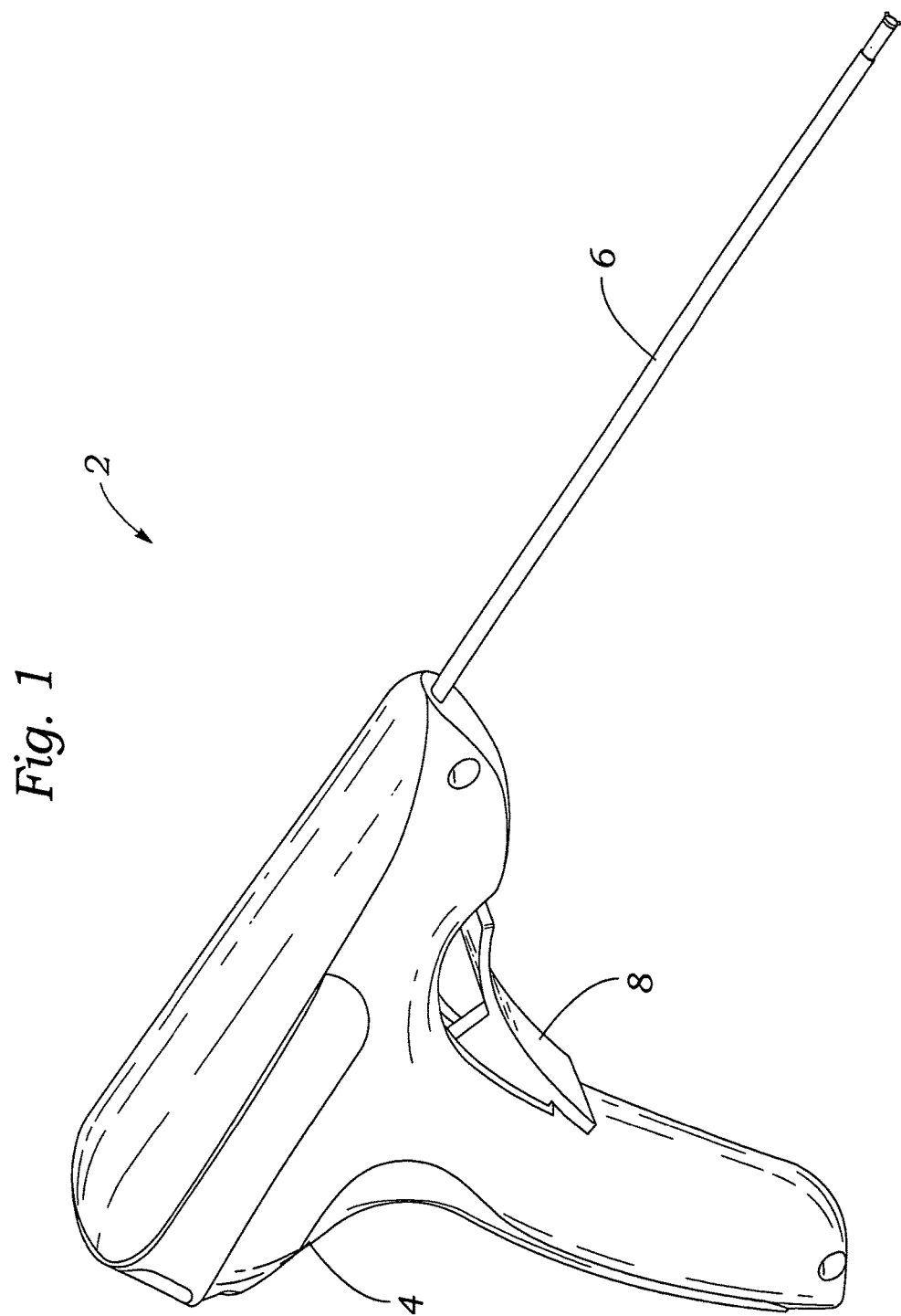
FIG. 1 shows an exemplary suture clip delivery device.

As shown in FIG. 1, the device 2 comprises a handle portion 4 that can be held and actuated by a user and a shaft portion 6 that can be inserted into the body, at least partially, to deploy suture clips onto sutures in hard to reach regions within the body in a minimally invasive manner. The handle portion 4 includes an actuator, or trigger, 8 that can be depressed by a user to deploy a suture clip onto one or more sutures and cut of the free end of the sutures. Releasing the actuator 8 can cause another suture clip loaded in the device 2 to move forward and be ready for deployment the next time the actuator is depressed. The distal end of the shaft portion 6 is not shown in FIG. 1. The device 2 can be used with any suitable suture clips, such as the suture clips 18 described herein or their equivalents.

The disclosed suture clip delivery devices can be used for many different procedures where sutures are used, such as to secure an artificial heart valve or other prosthetic device with the heart, to repair or treat native organs or tissues, to close openings or occlude lumens within the body, or for other procedures. Additional information regarding procedures for which the disclosed suture clip delivery devices can be used, and other information regarding exemplary suture clips and suture clip delivery devices, are disclosed in the following references, the entire contents of which are expressly incorporated by reference herein: U.S. Pat. Nos. 6,626,930; 7,094,244; 7,083,628; and 7,381,210; and U.S. Patent Application Publication Nos. 2007/0005079 and 2013/0165953.

Figure 2:
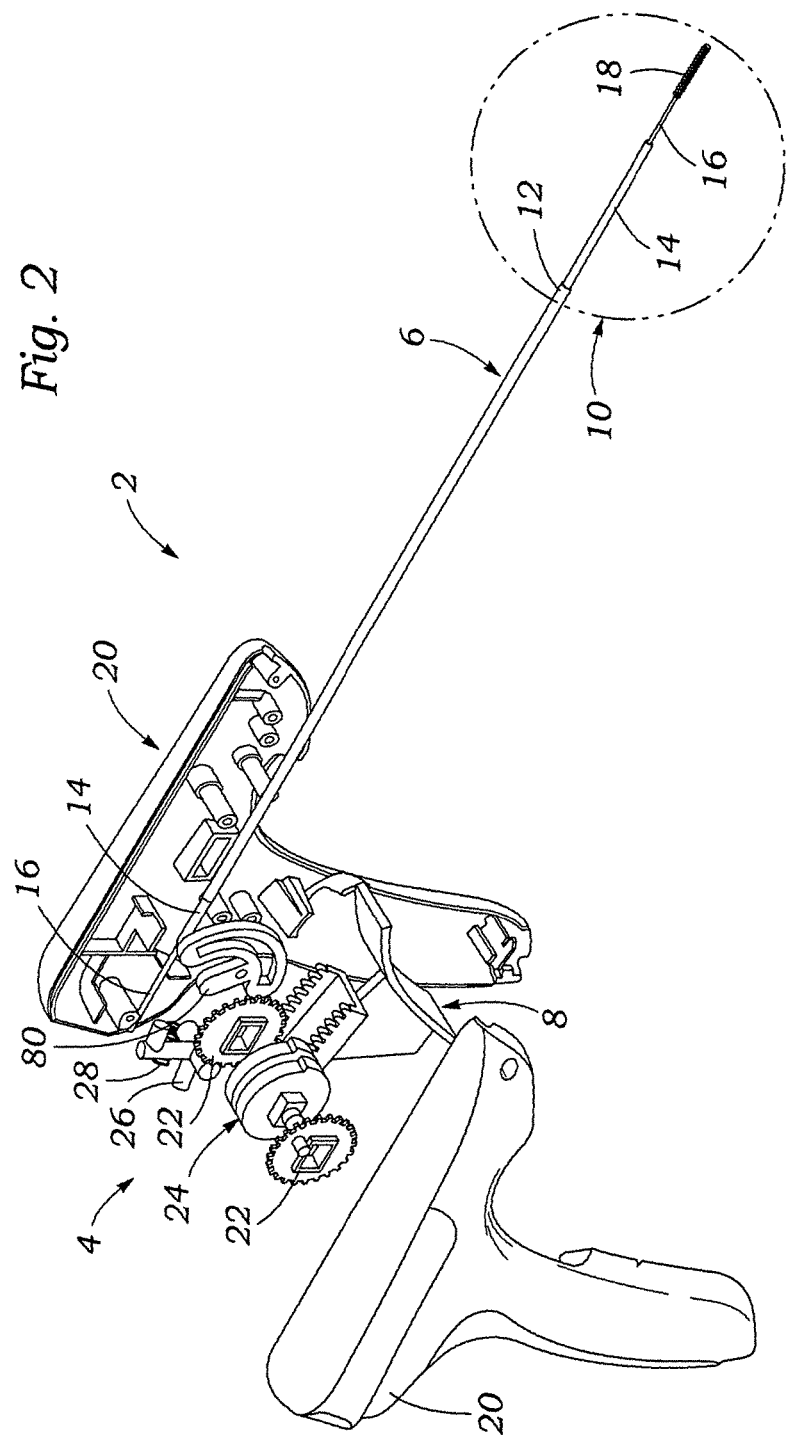
FIG. 2 is an exploded view of the device of FIG. 1.

FIG. 2 is an exploded view of the device 2. The distal portion 10 of the shaft portion 6 is shown at the right of FIG. 2, and is further illustrated in FIGS. 3-5. The shaft portion 6 includes a tubular outer shaft 12 that is fixed at its proximal end to the housing 20 of the handle portion, a suture clip retainer 14 that positioned within the outer shaft 12, a clip support mandrel 16 positioned within the retainer 14, and a plurality of suture clips 18 mounted on the mandrel 16 within the retainer 14.

As shown in more detail in FIGS. 11-19, the handle portion 4 includes left and right portions of a housing 20, the actuator 8, gears 22, cam 24, cam follower 26, follower spring 28, and bracket 80. While the actuation of the device 2 is described in more detail below, the following brief summary is provided here. Depressing the actuator 8 rotates the gears 22 and cam 24, which causes the cam follower 26 to move proximally (rearwardly), pulling the mandrel 16 proximally along with the cam follower. The rotation of the gears 22 can also turn the bracket 80, which causes the retainer 14 to rotate. Rotation of the retainer 14 cuts off free ends of the sutures to which a suture clip 18 is secured and also releases the tabs of the suture clips from notches in the retainer so that the clips can slide distally through the retainer after each suture clip is deployed. Releasing the actuator 8 then allows the spring 28 to push the cam follower 26 and support mandrel 16 distally, and also rotates the cam 24, gears 22, and bracket 80 in the opposite direction, causing the retainer to rotate back to its original position. The Actuator 8 can pivot about a point 84 near the bottom of the handle and be biased forward with a spring or the like.

Figure 3:
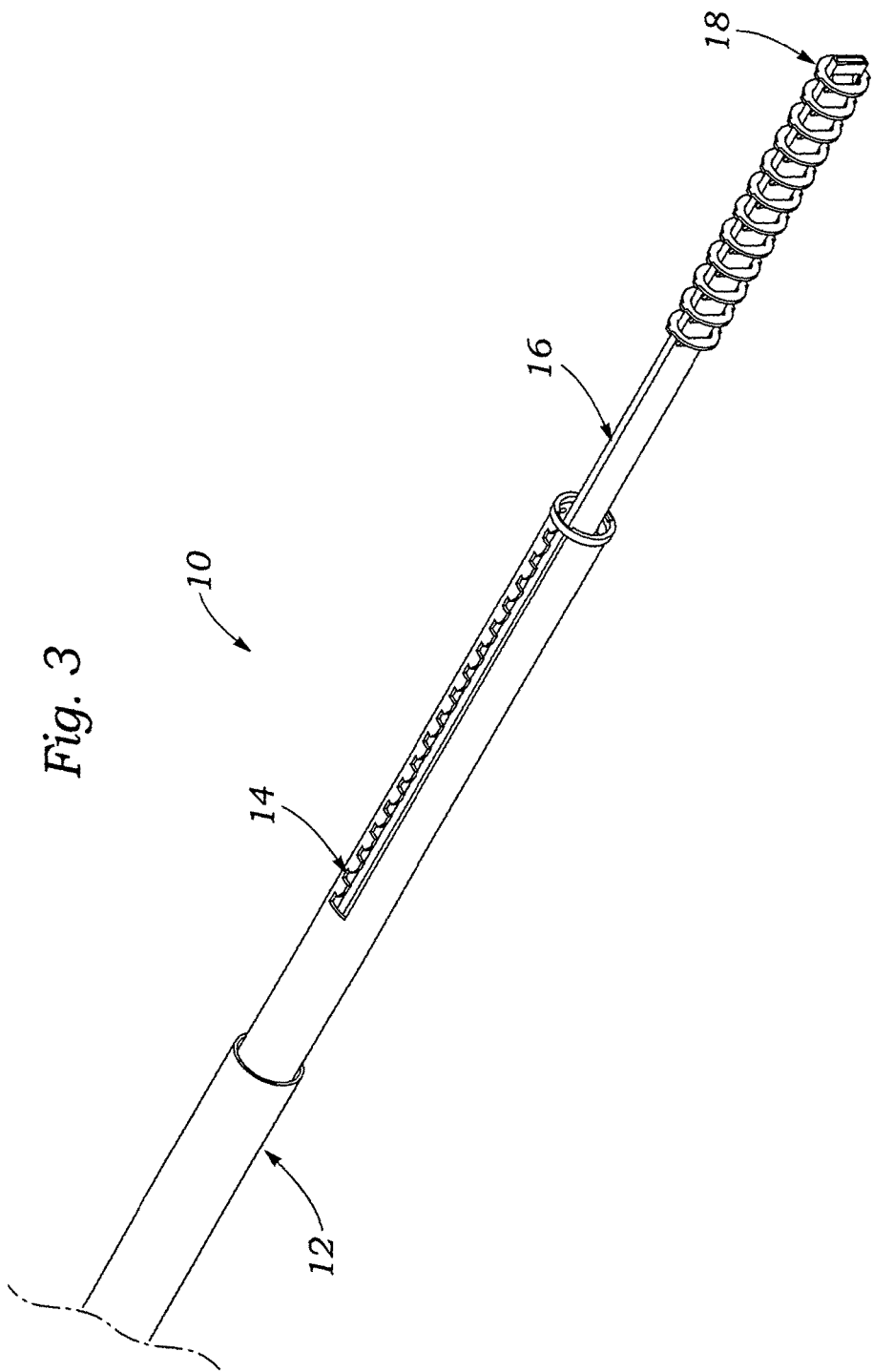
FIG. 3 is an enlarged view of a distal portion of FIG. 2, showing an exploded view of a distal end of a shaft portion of the device loaded with several suture clips.
Figure 7:
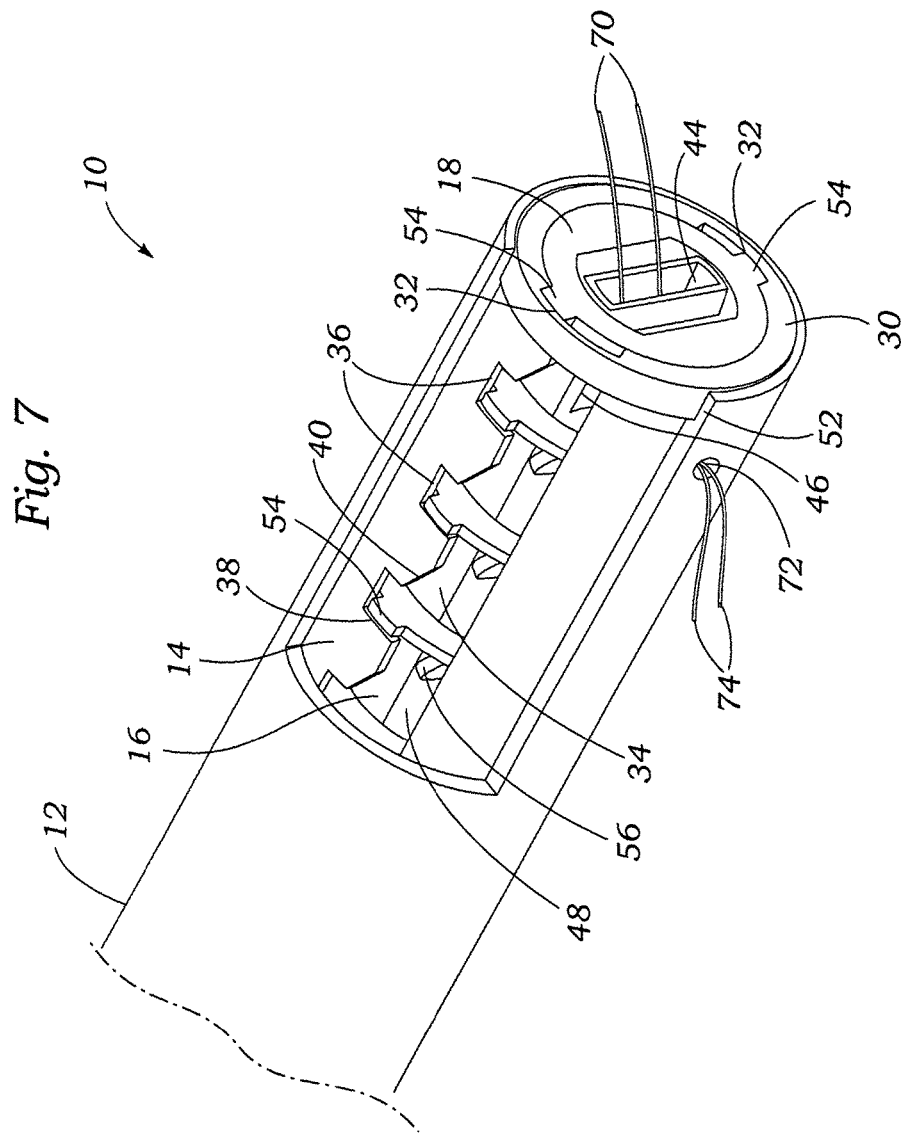
FIG. 7 shows a distal end of the delivery device of FIG. 1 showing sutures inserted into device and ready for delivery of a suture clip onto the sutures.

FIG. 3 shows the distal end of the shaft portion 6 with the various components exploded, though the outer shaft 12, retainer 14, and mandrel 16 all terminate with their distal ends at about the same axial position in the assembled device, as shown in FIG. 7.

Figure 4:
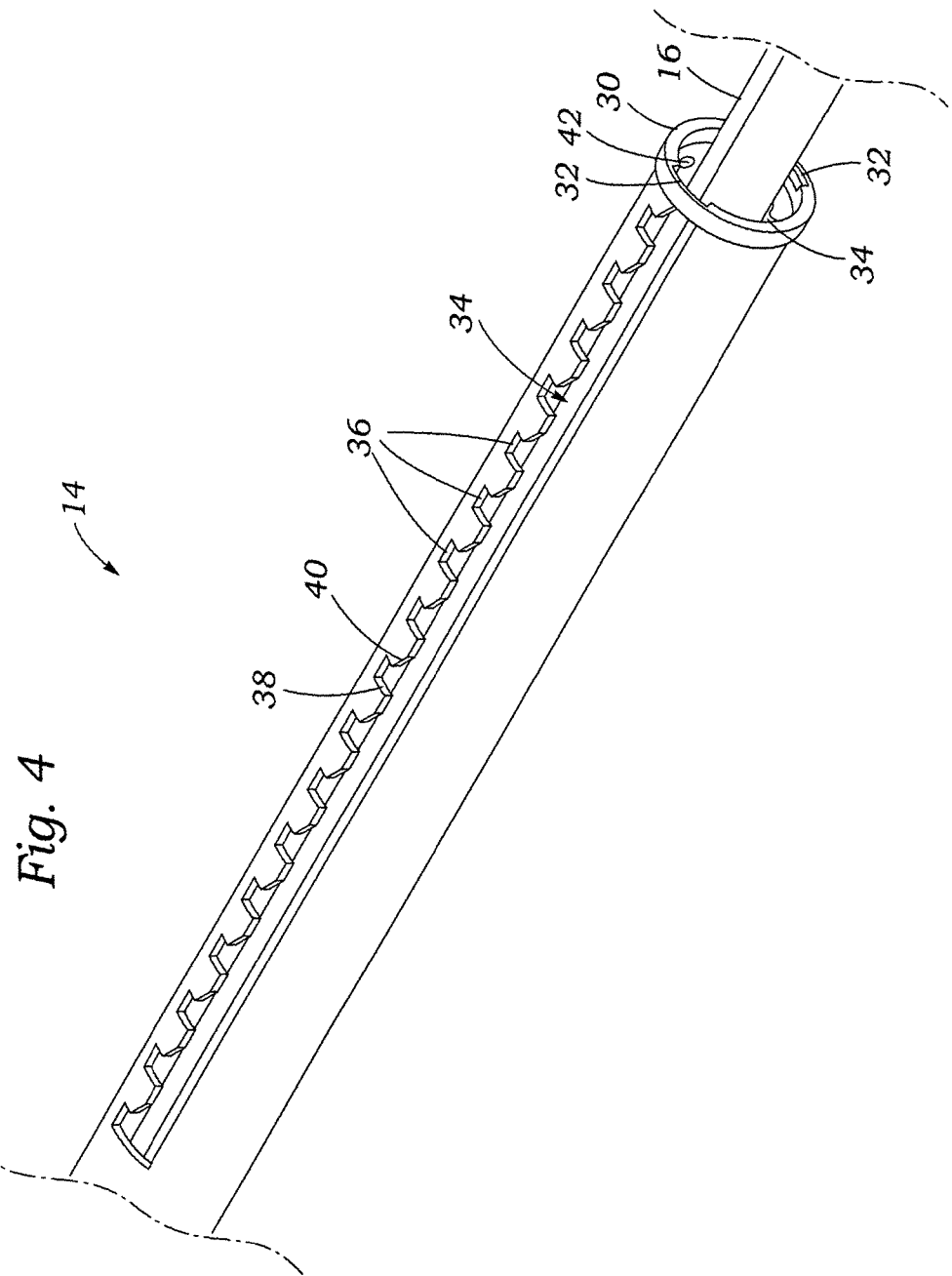
FIG. 4 is an enlarged view of a portion of FIG. 3 showing a suture clip retainer.

The distal end of the retainer 14 is shown in more detail in FIG. 4. The retainer 14 also includes a proximal portion that extends through the outer shaft 12 and into the handle portion 4, and is coupled to the actuation mechanism so that the retainer can be rotated about the shaft axis when the actuator 8 is depressed. The retainer 14 is generally tubular and includes an inner lumen through which the mandrel 16 extends. The distal end of the retainer, as shown in FIG. 4, includes an annular distal collar 30 and one or more elongated slots 34 that extend proximally from behind the collar 30. Each of the slots 34 includes a plurality of notches 36 at regularly spaced intervals along the axial length of the slot. In the illustrated example, the retainer 14 includes two slots 34 on diametrically opposite sides of the retainer. The number, size, and spacing of the slots 34 can correspond to the configuration of the suture clips that the device can be used with. For example, the suture clips 18 (see FIGS. 5 and 6) include two opposing tabs 54 that correspond with the two opposing slots 34 in the retainer. In other embodiments, suture clips with only one tab may be used, and a corresponding retainer with one slot 34 can be used. In still other embodiments, suture clips with three or more tabs can be used with a retainer that has a corresponding number of slots in a corresponding angular orientation. Similarly, the number of the notches 36 can correspond to the number of suture clips 18 that can be loaded into the device. In various embodiments, the retainer 14 can have any number of notches 36 along each slot 34 to allow the device to be loaded with a corresponding number of suture clips.

Figure 5:
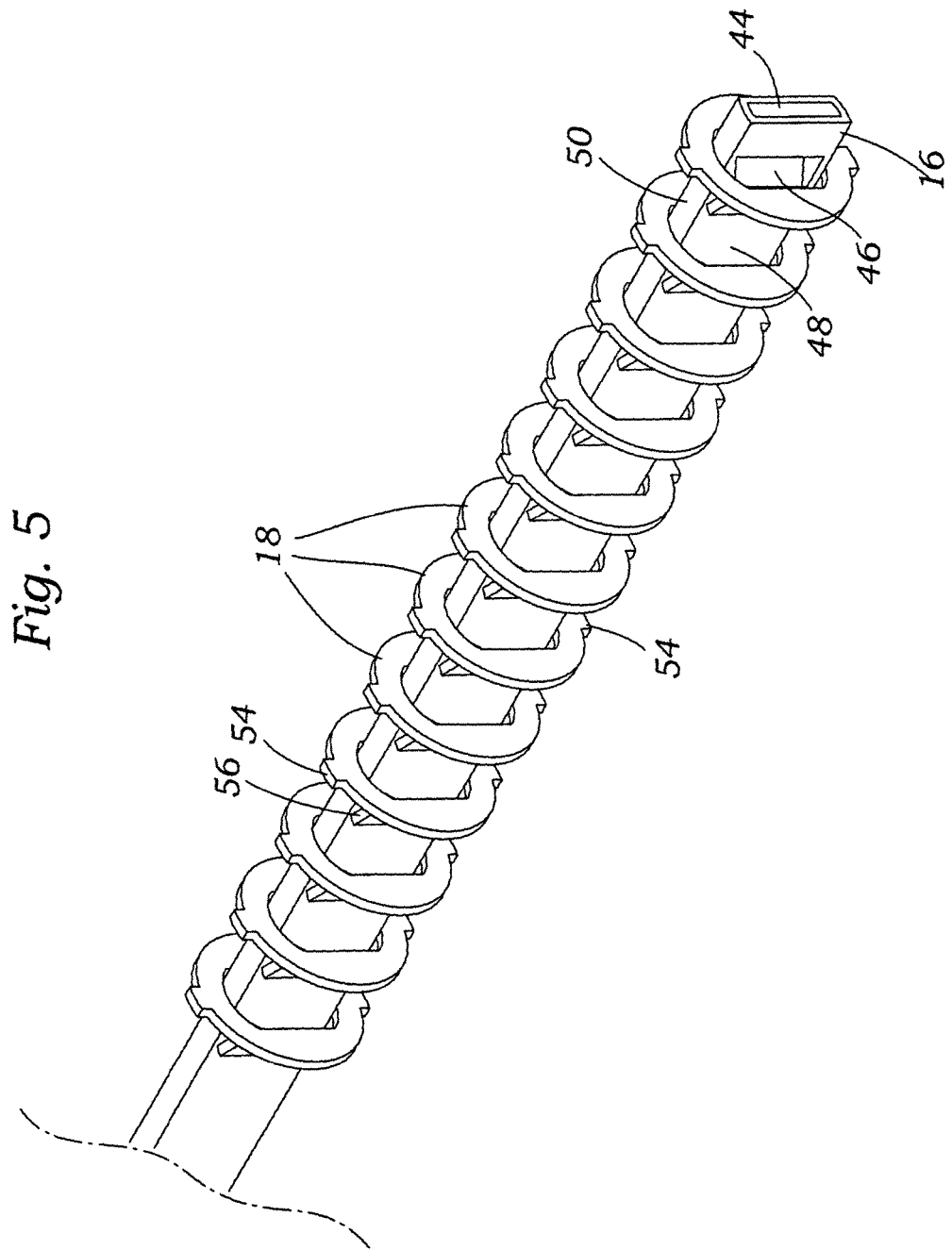
FIG. 5 is an enlarged view of a portion of FIG. 3 showing a support mandrel supporting several suture clips.

FIG. 5 shows the distal end of the mandrel 16 with several suture clips 18 loaded on it. The mandrel 16 can have a generally rectangular cross-sectional shape, as shown, or other non-circular cross-sectional shapes. The mandrel 16 can also include an inner lumen 44 that extends at least partially through the mandrel from the distal end of the mandrel. In some embodiments, the inner lumen extends all or most of the way through the mandrel 16 with a proximal exit within or adjacent the handle portion 4. The mandrel 16 can also include a lateral opening 46 near the distal end of the mandrel that communicates with the inner lumen 44.

The mandrel 16 has an outer profile that is shaped to fit through the suture clips 18 with a friction fit as shown in FIG. 5. When loaded on the mandrel 16, the suture clips are resiliently deformed such that they pinch onto the sides 48 of the mandrel while the top and bottom surfaces 50 of the mandrel can be positioned closely with inner surfaces of the suture clips to keep them snuggly supported on the mandrel with minimal play allowed in the directions perpendicular to the shaft axis.

Figure 6:
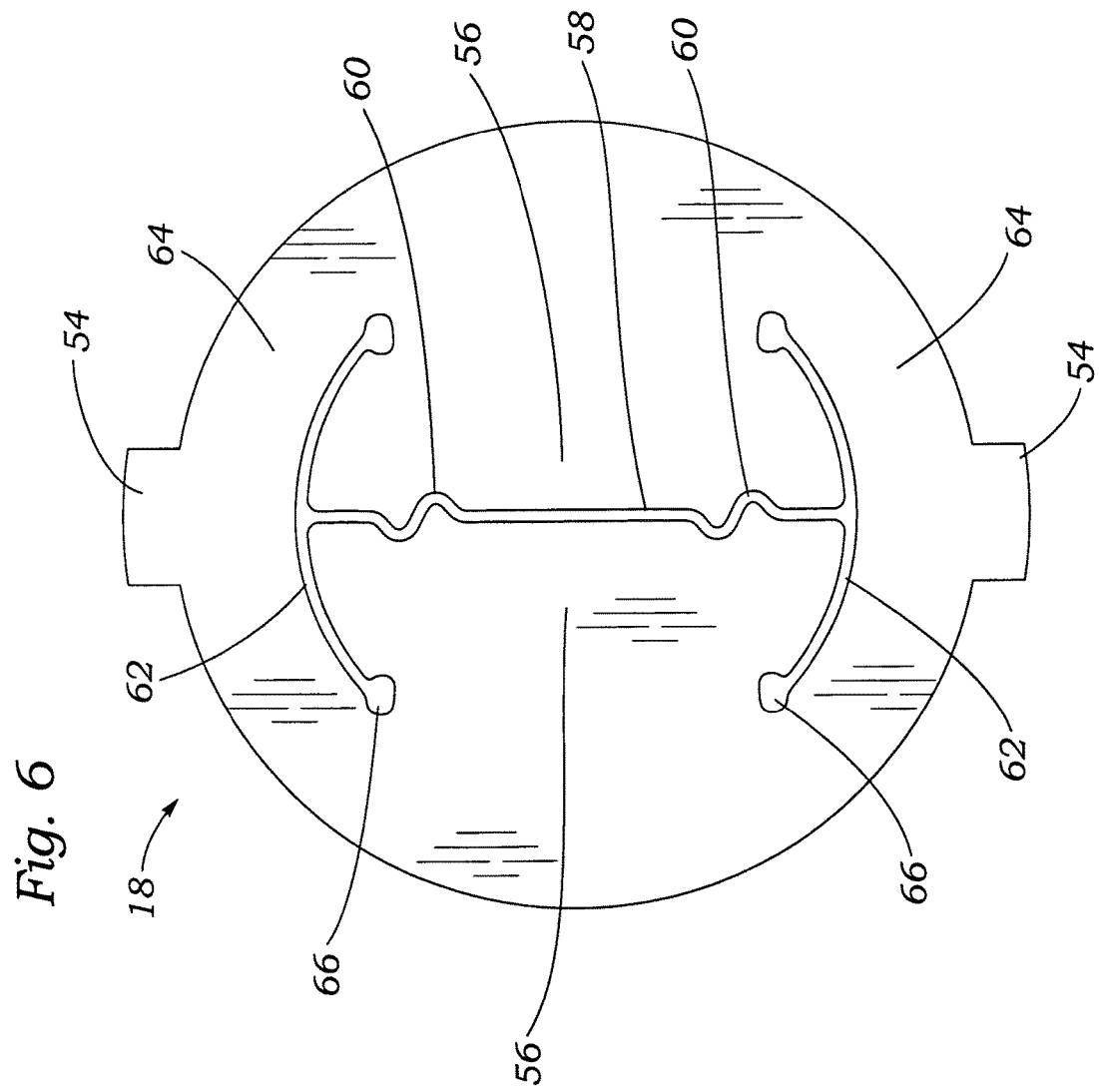
FIG. 6 is a plan view of an exemplary suture clip that can be used with the disclosed delivery devices.

FIG. 6 is a plan view of an exemplary suture clip 18. The clip 18 has a thin thickness, or depth, (dimension perpendicular to the page in FIG. 6) relative to its major dimension, or diameter. The thickness can be relatively uniform for the whole clip, and can be substantially smaller relative to the diameter of the clip (left-to-right dimension in FIG. 6), such as less than 25% of the diameter, less than 15% of the diameter, less than 10% of the diameter, and/or less than 5% of the diameter.

The clip 18 is generally disk shaped with two suture engagement flaps 56 that project inwardly toward each other and define a suture engagement slot 58. The suture engagement slot 58 can include a tortuous portion 60 at either end to prevent sutures that are pinched between the flaps 56 in the suture engagement slot 58 from sliding laterally out of the slot 58 into either of the arcuate slots 62 that extend from the ends of the slot 58. The arcuate slots 62 space the flaps 56 from an outer annular portion 64 of the clip 18 and allow the flaps 56 to articulate out of the plane of FIG. 6 while the outer annular portion 64 stays generally in or near the plane of the FIG. 6. The arcuate slots 62 can include enlarged, rounded end portions 66 that reduce stress concentrations in the clip material around them when the flaps 56 are resiliently deformed out of plane. FIG. 6 also shows two tabs 54 at diametrically opposite sides of the clip 18.

The suture clips 18, and other suture clip embodiments, can be made from a variety of materials including, for example, nickel-titanium alloys, shape-memory alloys, stainless steel, titanium, various plastics, and other biologically-compatible materials. Exemplary suture clips can be formed from shape memory and/or pseudoelastic materials such as nitinol. In some embodiments, the suture clips can be formed from nitinol (e.g., with an alloy of nickel at 54.5-57% by weight with titanium accounting for the balance except for residual amounts (less than 0.05% each) of oxygen, carbon, and hydrogen) or another shape memory and/or pseudoelastic material, with the suture clips formed so that the clip assumes its closed position (e.g., the flat position shown in FIG. 6) when in the austenite condition (i.e., when generally unstressed at body temperature). The nitinol can have an austenite finish temperature selected to match the particular application. For example, an austenite finish temperature of −5 degrees to +15 degrees Celsius may be selected.

Figure 8:
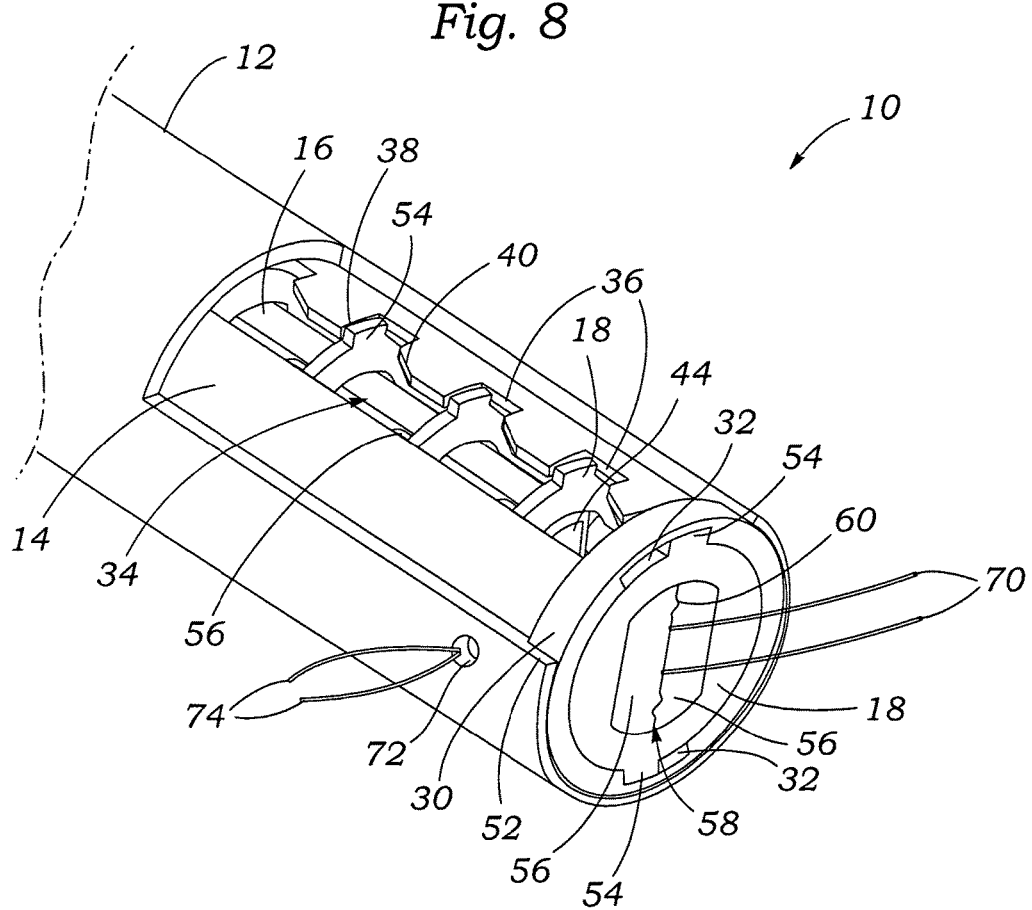
FIG. 8 shows the distal end of the delivery device with sutures inserted into device and the support mandrel retracted to cause a distal-most suture clip to be deployed onto the sutures.

A suture clip can be formed from material that will assume its martensite condition when subjected to sufficient stress, such as the stress applied to the clip's engagement flaps 56 and annular outer body 64 when the suture clip is mounted onto the mandrel 16, as shown in FIG. 5. In such an embodiment, the mandrel 16 applies stress to the engagement flaps 56, forcing the engagement flaps to open wide enough to receive the mandrel through the slot 58. The stressed material, including the bent material where the engagement flaps 56 join the annular outer body 64, is forced into its martensite condition. When the stress is removed, such as when the mandrel slides out from the distal-most clip 18, as depicted in FIG. 8, the material returns to its austenite condition so that the annular outer body 64 and the engagement flaps 56 assume their flat shape shown in FIG. 6.

When the clips 18 are loaded onto the mandrel 16, as shown in FIG. 5, the flaps 56 are resiliently deformed out of plane and the slot 58 enlarges wide enough to accommodate the width of the mandrel. The clips 18 are loaded on the mandrel 16 with the flaps 56 projecting proximally, as shown, such that the clips can more readily slide distally along and off of the mandrel. Having the flaps 56 extend proximally also allows the distal-most clip 18 to be positioned with the outer annular portion 64 and flaps 54 at the distal end of the mandrel when ready for deployment, as shown in FIG. 7.

The clips 18 when loaded on the mandrel 16 can be spaced apart at regular axial intervals that correspond to the axial spacing of the notches 36 in the axial slots 34 of the retainer 14 (see FIG. 4). When the device 2 is assembled with the clips 18 loaded, as illustrated in FIG. 7, the tabs 54 of the clips are positioned in respective ones of the notches 36 and adjacent to or touching the proximal surfaces 38 of the notches. As shown in FIG. 7, the distal-most clip 18 can be positioned with its tabs 54 in recesses 32 formed in the distal collar 30 of the retainer 14. The recesses 32, like the surfaces 38, provide a backstop behind the tabs 54 that block the clips 18 from moving proximally relative to the retainer, but allow the clips to move distally relative to the retainer.

FIG. 7 shows the distal end of the shaft portion 6 of the device 2 in a position ready to deploy the distal-most clip 18 onto sutures 70. The sutures 70 have been direct into a position where they extend into the inner lumen 44 of the mandrel 16, out through the lateral opening 46 of the mandrel, through a lateral opening 42 in the retainer 14, and through a lateral opening 72 in the outer shaft 12. These lateral openings can be generally aligned in this configuration. The free ends 74 of the sutures are shown projecting from the lateral opening 72 in the outer shaft 12 in FIG. 7. The lateral opening 42 in the retainer 14 is shown in FIG. 4. The lateral opening 42 can alternatively be located on the opposite side of the retainer from where it is shown in FIG. 4, between the symmetrical slots 34 on opposite sides of the retainer. In the configuration shown in FIG. 7, the lateral openings 46, 42 and 72 are aligned so the sutures 70 can be passed through them. Passing the sutures through the openings 46, 42, and 72 can be performed in any suitable manner, such as by using a snare to pull the sutures through the openings. Passing the sutures through the lateral openings 46, 42, 72 positions the distal-most clip 18 around the sutures 70, but the distal-most clip is not yet secured onto the sutures. The free ends 74 of the sutures can then be grasped and a desired tension can be applied to the sutures 70 with the distal end of the shaft portion 6 and the distal-most clip 18 being positioned adjacent to the location where the sutures 70 exit from tissue, a prosthetic device, or other substrate.

Once a desired positioning of the distal-most clip 18 relative to the sutures 70 is obtained and a desired tension is applied to the sutures 70, the distal-most clip can be deployed onto the sutures 70. As shown in FIG. 8, to deploy the distal-most clip 18 onto sutures, the actuator 8 of the device 2 is depressed to cause the mandrel 16 to move proximally relative to the shaft portion 6 and the clips 18. As the mandrel 16 moves proximally, the tabs 54 of the clips 18 carried on the mandrel contact the proximal surfaces 38 of the notches 36 of the retainer 14 and the proximal surface of the recess 32 in the collar 30 to prevent the clips from moving proximally with the mandrel. This causes the mandrel 16 to slide through the clips 18 while the clips are held relatively stationary. The mandrel 16 moves proximally about the distance of one interval between two adjacent clips. As shown in FIG. 8, the mandrel 16 has moved proximally such that the distal end of the mandrel is now in line with the second-most distal clip 18. When the mandrel exits the distal-most clip, the flaps 56 of the distal-most clip 18 resiliently close back to the flat position (FIG. 6) and pinch the sutures 70, as shown in FIG. 8. The sutures are desirably engaged in the portion of the slot 58 between the two tortuous portions 60 (see FIG. 6).

Figure 9:
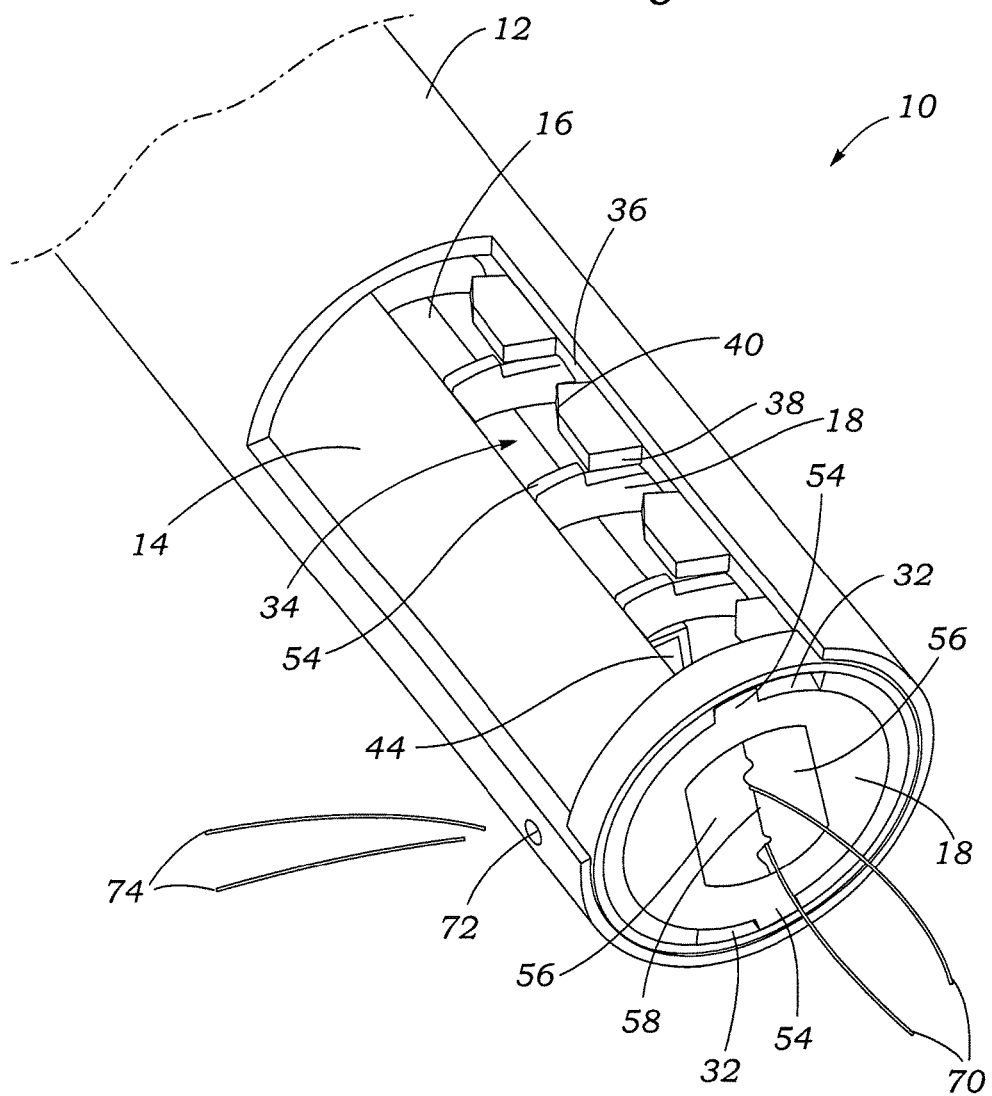
FIG. 9 shows the distal end of the delivery device with the suture clip deployed onto the sutures and the clip retainer rotated to cut off free ends of the sutures and release the suture clips from the retainer.

As shown in FIG. 9, depression of the actuator 8 can also cause the retainer 14 to rotate about the shaft axis relative to the outer shaft 12, the mandrel 16, the clips 18, and the rest of the device 2. This rotation can occur after the proximal motion of the mandrel or the two motions can overlap in time. For example, the rotational motion of the retainer can begin while the proximal motion of the mandrel in partially complete. The rotational motion of the retainer 14 can have two effects. First, the shearing motion between the lateral opening 42 of the retainer and the lateral opening 72 of the outer shaft can cut off the free ends 74 of the sutures 70. Second, the rotational motion of the retainer 14 causes the tabs 54 of the clips 18 to exit the notches 36 of the retainer and become positioned in the open parts of the axial slots 34 (FIG. 9). This allows the clips 18 to then move axially relative to the retainer 14 as the tabs 54 can travel along the axial slots 34. At the distal end of the retainer 14, the tabs 54 of the distal-most clip 18 also move angularly about the recesses 32 in the collar 30.

With the free ends 74 of the sutures cut off and the distal-most clip 18 secured onto the sutures 70, the device 2 can be retract from the clip deployment site, allowing the distal-most clip to exit the distal end of the device and remain secured to the sutures at the deployment site.

Figure 10:
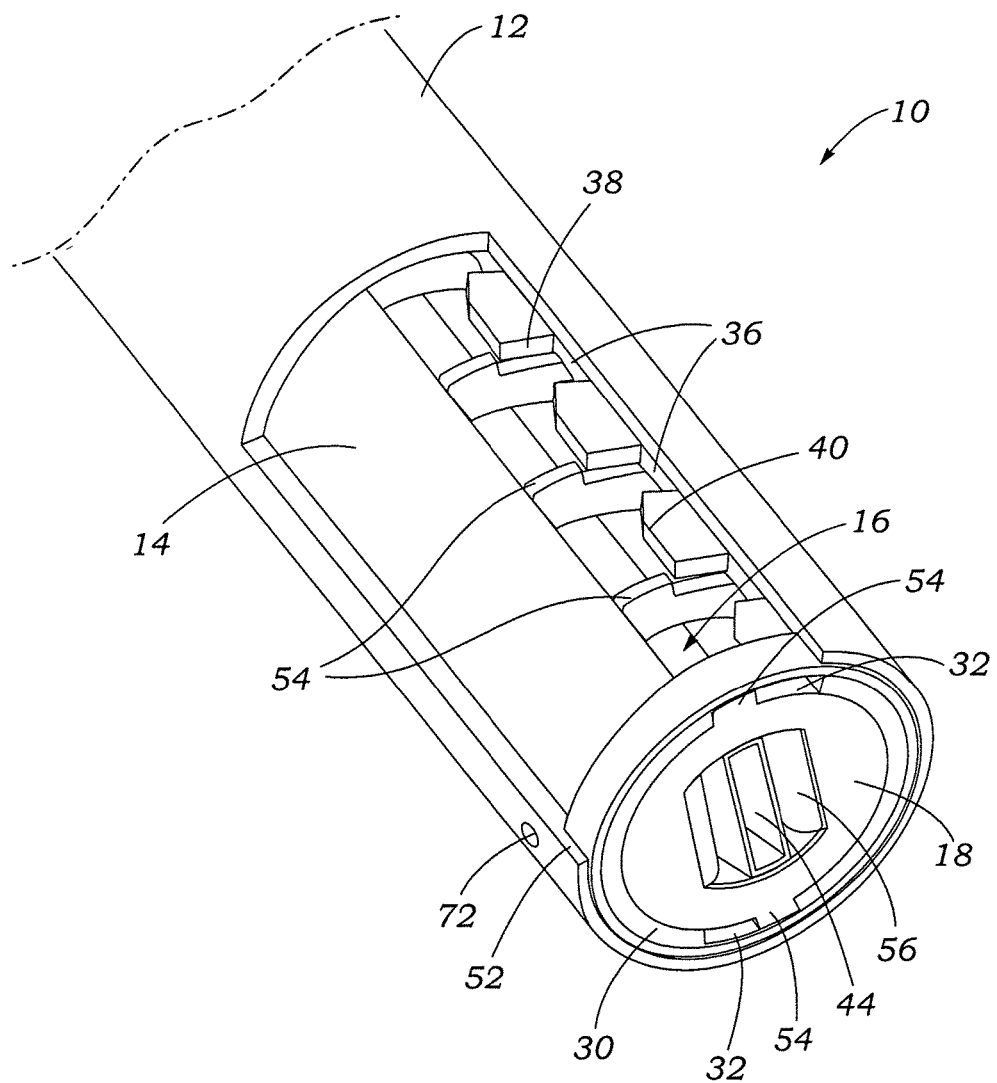
FIG. 10 shows the distal end of the delivery device after the distal-most suture clip has been deployed onto the sutures and has be removed from the delivery device, and after the support mandrel has been advanced again to advance the remaining suture clips such that the next most distal suture clip is ready to be deployed onto another suture or sutures.

As shown in FIG. 10, when the actuator 8 is released after a suture clip has been deployed, the mandrel 16 moves distally relative to the retainer 14 and the outer shaft 12, and the mandrel carries the remaining clips 18 distally along with it as the tabs 54 travel distally along the axial slots 34 in the retainer. The notches 36 can optionally include an angled or rounded distal surface 40 to facilitate the tabs 54 moving distally from adjacent one notch 36 to adjacent the next notch 36. The distal surfaces 40 can reduce the risk of the tabs 54 getting caught on the corners of the notches as the clips slide distally through the slots 34. The formerly second-most distal clip 18 then becomes located at the distal end of the shaft inside the collar 30. Releasing the actuator 8 also causes the retainer to rotate back the opposite direction, returning to its original position. As the retainer rotates, the tabs 54 move back into the notches 36, and the device returns to the ready position shown in FIG. 7, without the sutures 70. The process illustrated in FIGS. 7-10 can then be repeated to deploy the remaining suture clips 18 to other sutures.

FIGS. 12-15 are perspective views of the actuation mechanism in the handle portion 2 showing four stages of the actuation sequence, which correspond generally with the four configurations shown in FIGS. 7-10. FIGS. 16-19 are side views of the actuation mechanism that correspond to the perspective views shown in FIGS. 12-15.

In the position shown in FIGS. 12 and 16, the actuator 8 is in its forward position and not depressed. The mandrel 16 and the retainer 14 are in the position shown in FIG. 7. In this position, the cam follower 26 in its forward or distal position and the following spring 28 attached to a proximal aspect 102 of the cam follower is not compressed or is in its minimally compressed state. The proximal end of the mandrel 16 is fixed to a distal aspect 100 of the cam follower 26. The proximal end of the retainer 14 extends into the handle portion 4 and includes a radial projection 104 that extends into a circumferential slot 106 in the bracket 80. In the view of FIG. 16, the bracket 80, gears 22, and cam 24 are in their most clockwise rotational position, in which a first end 108 of the slot 106 is adjacent to or contacting the radial projection 104 of the retainer and a portion of the cam's radial bearing surfaces 96 with a minimum radius is in contact with the cam follower's lateral aspects 98.

Figure 11:
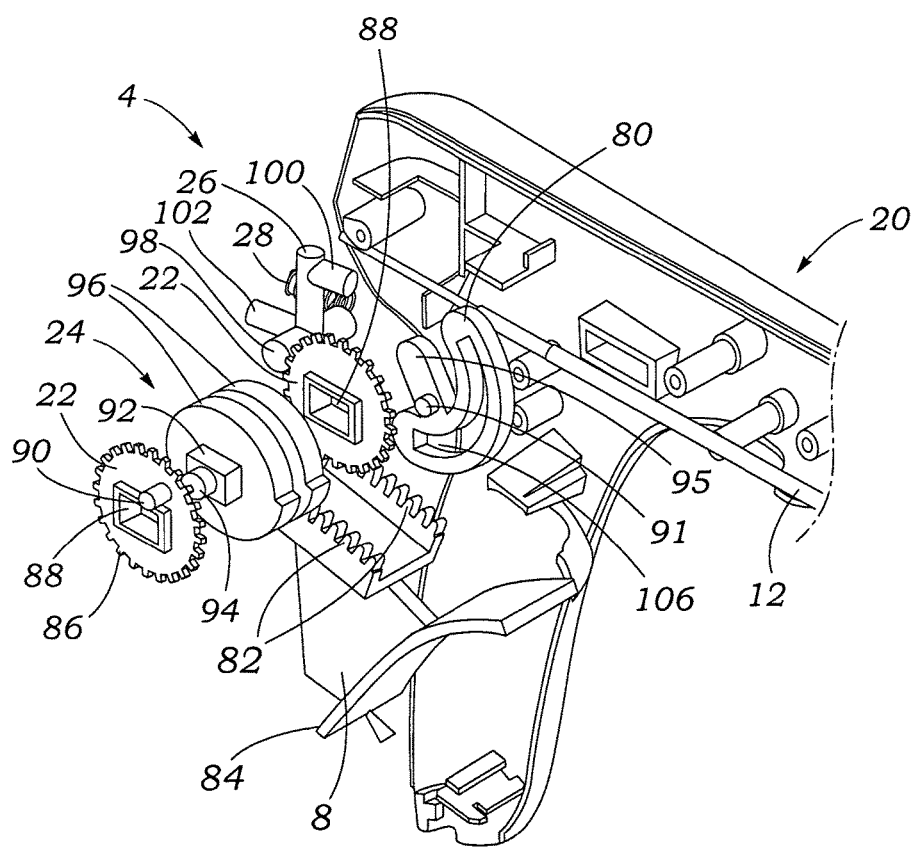
FIG. 11 is an enlarged exploded view of a handle portion of the delivery device of FIG. 1.

With reference to FIG. 11, the cam 24 includes rectangular (or other shaped) lateral pegs 92 on either side that fit into correspondingly shaped openings 88 in the gears 22, which fixes the rotational motion of the cam 24 to that of the gears 22. The cam 24 further includes lateral projections 94 (e.g., cylindrical shaped as shown) on either side of the rectangular projections, one of which fits through an opening 95 in the bracket 80, and which lateral projections 94 are rotationally engaged with the handle housing 20 to allow the cam to rotate but not translate perpendicular to its rotational axis.

One or both of the gears 22 can also include a lateral projection 90 that is offset radially from the gear's rotation axis and which lateral projection 90 fits into a hole 91 in the bracket 80 to fix the bracket's rotational motion to that of the gears 22 and the cam 24. When the actuator 8 is depressed (moves to the right in FIG. 16), the actuator's upper teeth 82, which are engaged with the teeth 86 of the gears 22, cause the gears, cam, and bracket to rotate in a corresponding manner (counter-clockwise in FIG. 16).

As shown in FIGS. 13 and 17, when the cam 24 rotates counter-clockwise, the cam's radial bearing surfaces 96 slide across the later aspects 98 of the cam follower 26, the portion of the radial bearing surfaces in contact in contact with the lateral aspects 98 gradually increases in radius, pushing the cam follower rearwardly (proximally) and compressing the spring 28. As shown in FIG. 13, the radial bearing surfaces 96 may increase in radius over a selected circumferential portion, such as between the lines marked 112 and 114. The circumferential portions of the radial bearing surfaces 96 beyond the lines 112 and 114 can have a continuous radius, with the portion to the left of line 112 in FIG. 13 having a smaller radius and the portion below line 114 having a greater radius. Thus, the cam follower 26 and the mandrel 16 only move axially when the region of the radial bearing surfaces 96 between the lines 112 and 114 are sliding across the lateral aspects 98. This can allow the mandrel 16 to remain axially still while further depression of the actuator 8 causes the bracket 80 to rotate the retainer 14, and vice versa. In the position of FIGS. 13 and 17, the cam follower 26 and mandrel 16 are at their maximally proximal position, but the retainer 14 has not begun to rotate yet, corresponding to the position shown in FIG. 8. In this position, the bracket 80 has rotated to cause the lateral projection 104 of the retainer 14 to traverse the slot 106 from the first end 108 (in FIGS. 12 and 16) to the second end 110 of the slot.

As shown in FIGS. 14 and 18, further depression of the actuator 8 and counter-clockwise motion of the bracket 80 causes the second end 110 of the slot 106 to pivot the lateral projection 104 downward about the shaft axis, rotating the retainer 14. During the rotation of the retainer 14, a uniform radius portion of the radial bearing surfaces 96 can be in contact with the cam follower 16, keeping the mandrel 16 stationary. FIGS. 14 and 18 show a maximum depression of the actuator 8, with maximum rotation of the retainer 14, which corresponds to the position shown in FIG. 9.

As shown in FIGS. 15 and 19, subsequent releasing of the actuator 8 causes (via resilient biasing forces applied to the actuator) the actuator to recoil back out of the housing 20 (to the left in FIG. 19) and causes the gears 22, cam 24, and bracket 80 to rotate clockwise. During the initial portion of this recoil motion, the bracket slot 106 moves over the lateral projection 104 without rotating the retainer 14, while at the same time the variable radius portion of the cam's radial bearing surfaces 96 slides over the lateral aspects 98 of the cam follower 26 to allow the compressed spring 28 to push the cam follower and mandrel back distally to their original position as in FIGS. 12 and 16. At the point shown in FIGS. 15 and 19, which corresponds to the position shown in FIG. 10, the mandrel 16 has moved back distally and the first end 108 of the bracket slot 106 contacts the lateral projection 104 and begins pivoting it upward, thereby rotating the retainer 14 back toward its original position. Further recoiling of the actuator 8 returns the mechanism back to the position shown in FIGS. 12 and 16, which corresponds to the position of FIG. 7.

Figure 21:
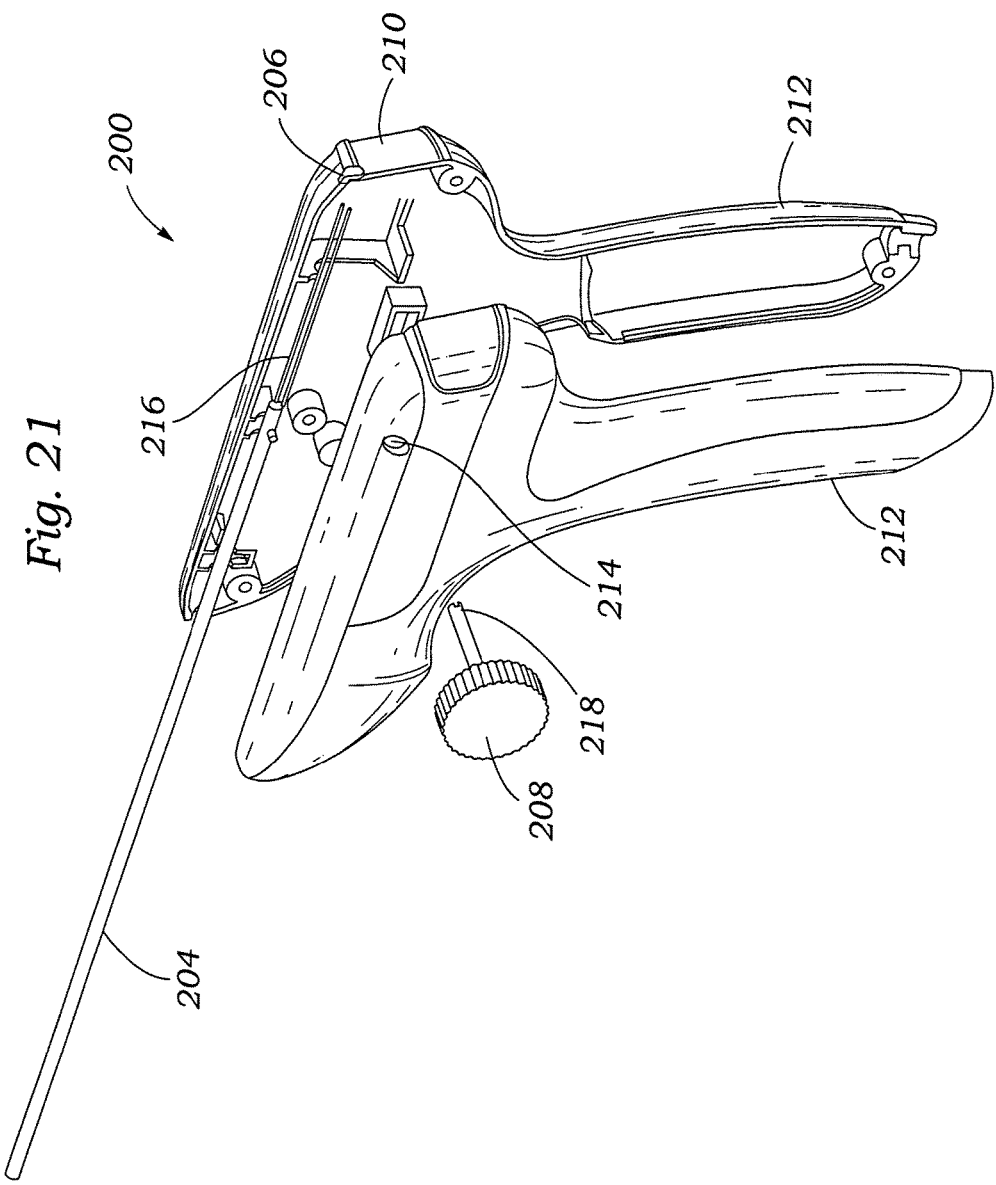
FIG. 21 is an exploded view of the device of FIG. 20, showing sutures extending entirely through the shaft. Sutures can be pulled out through the rear end of the device.

FIGS. 20-24 illustrate another suture clip delivery device 200 that can be loaded with a plurality of suture clips, such as the clips 18, and used to successively deploy plural clips onto sutures, similar to the device 2 disclosed herein. As shown in FIG. 20, the device 200 includes a handle portion 202 and a shaft portion 204. The shaft portion 204 can include an outer shaft, retainer, and mandrel similar to those described with device 2, except that in the device 200 the sutures are drawn all the way through the shaft and out through a proximal opening 206 in the handle portion, rather than out through a lateral opening in the shaft. The device 200 can also include a suture tensioner 208 that can be rotated to adjust the tension in the sutures, as well as a suture tension monitoring system with tension or torque display 210 on the handle. As shown in FIG. 21, sutures 216 are passed through the shaft portion 204, through a winding portion 218 in the suture tensioner 208, and out through the proximal opening 206. The suture tensioner 208 includes the winding portion 218, which passes laterally through an opening 214 in one side of the handle housing 212, and an external knob portion that can be manually rotated to wind the sutures 216 around the winding portion 218 until a desired tension is applied to the sutures. A sensor coupled to the tensioner 208 can measure the tension or torque applied and cause the tension/torque to be displayed on the display 210. Alternatively, a user can pull on the free ends of the sutures protruding from the opening 206 to adjust the tension.

Figure 22:
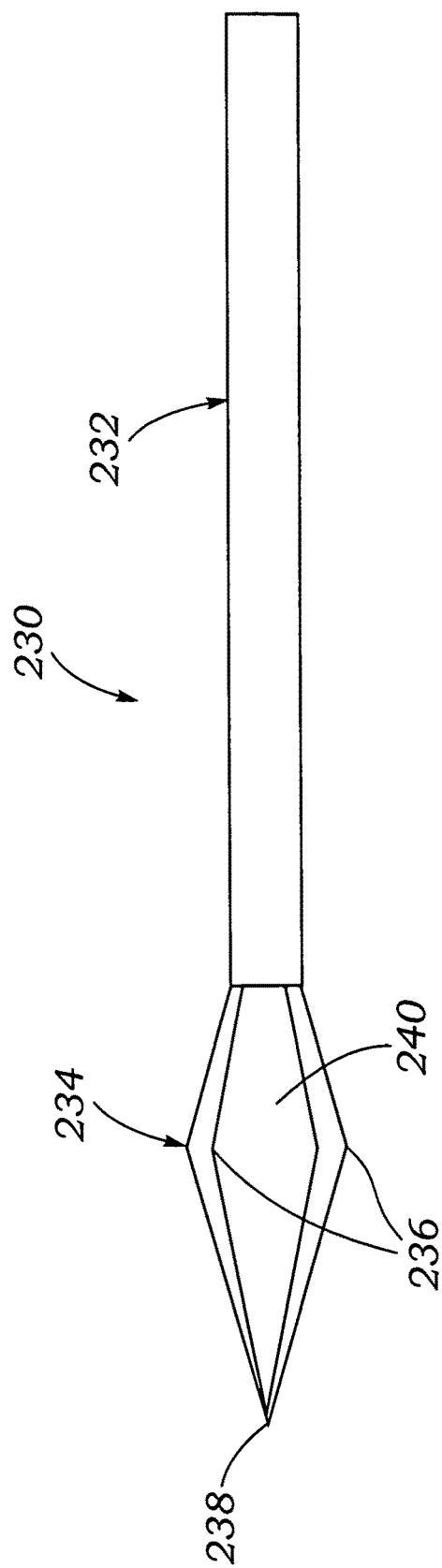
FIG. 22 shows an exemplary snare for pulling sutures through the device of FIG. 21.

FIG. 22 shows an exemplary snare 230 that can be used to pull the sutures 216 through the device 200. The snare 230 includes a rigid shaft 232 and a flexible loop 234 at the distal end of the shaft. The loop 234 can include angled portions 236 and 238 that allow the loop to resiliently bias apart toward the opening position shown, and then collapse to a flat shape to pass through the shaft of the device 200. The snare 230 can be passed through the device 200 with the collapsed loop 234 being inserted into the proximal opening 206, through the tensioner 208, and through the shaft portion 204 (e.g., through the mandrel 264, retainer 262, clips 272, and outer shaft 260) and out through the distal end of the device 266 (see FIG. 23). When the loop 234 exits the distal end of the device 200, the loop resiliently opens to form opening 240. Sutures can then be passed through the opening 240. Retracting the snare 230 proximally back through the device 200 then causes the loop 234 to collapse and capture the sutures as the sutures are pulled through the device and out through the proximal opening 206. The snare can then release the sutures.

Once sutures are loaded through the device 200, the device can be advanced over the sutures distally toward the location where the sutures exit the tissue or other material to locate the distal-most suture clip adjacent that location. Desired tension can then be applied to the sutures by rotating the tensioner knob 208 and/or pulling on the free ends of the sutures. The distal-most suture clip can then be deployed onto the sutures using an actuation mechanism similar to that shown in FIGS. 7-19. However, the device 200 can cut off the free ends of the sutures using a heating element located at the distal end of the shaft rather than using the shearing motion between the retainer and the outer shaft as in the device 2.

Figure 23:
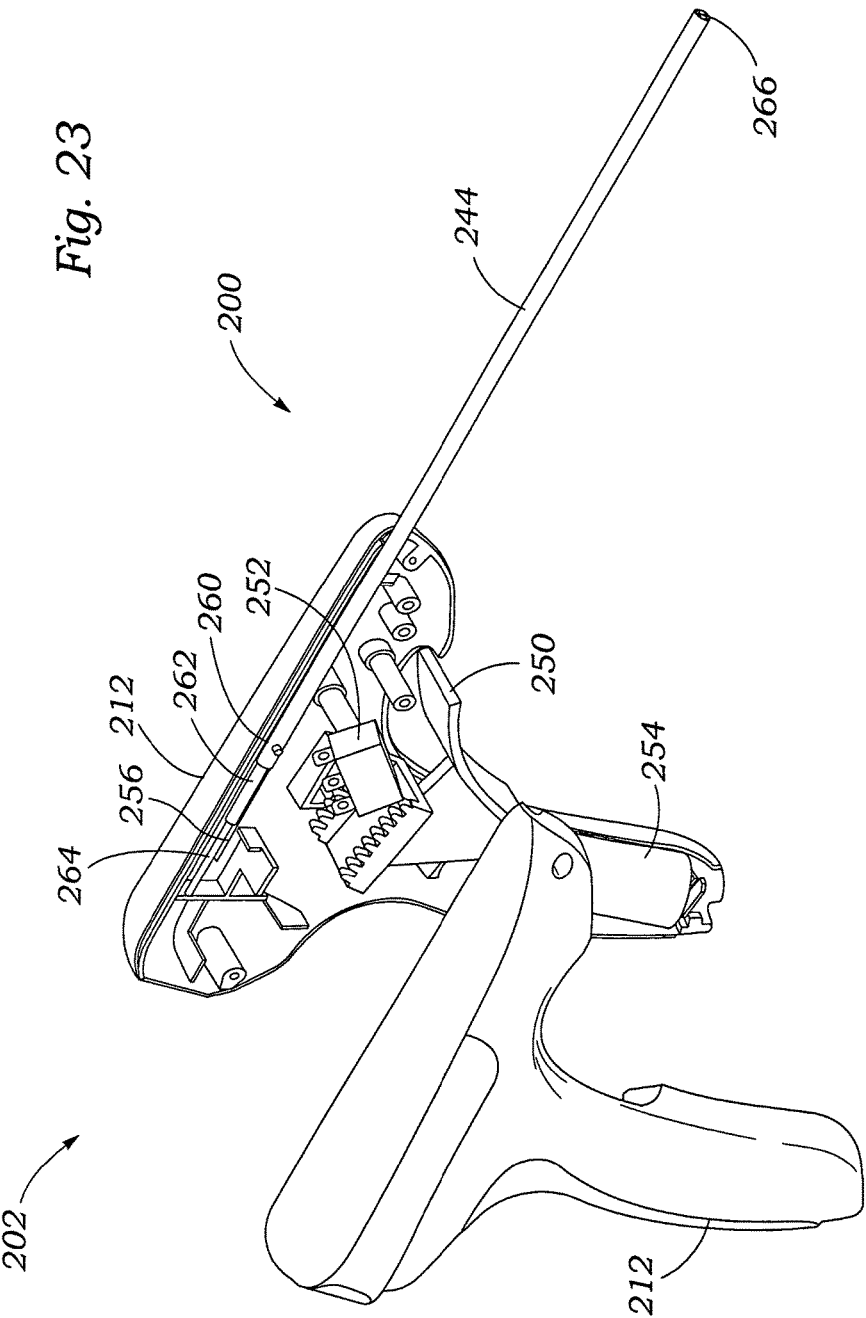
FIG. 23 is an exploded view of an exemplary suture clip deployment device that includes an electrically powered heating system for cutting sutures using heat.
Figure 24:
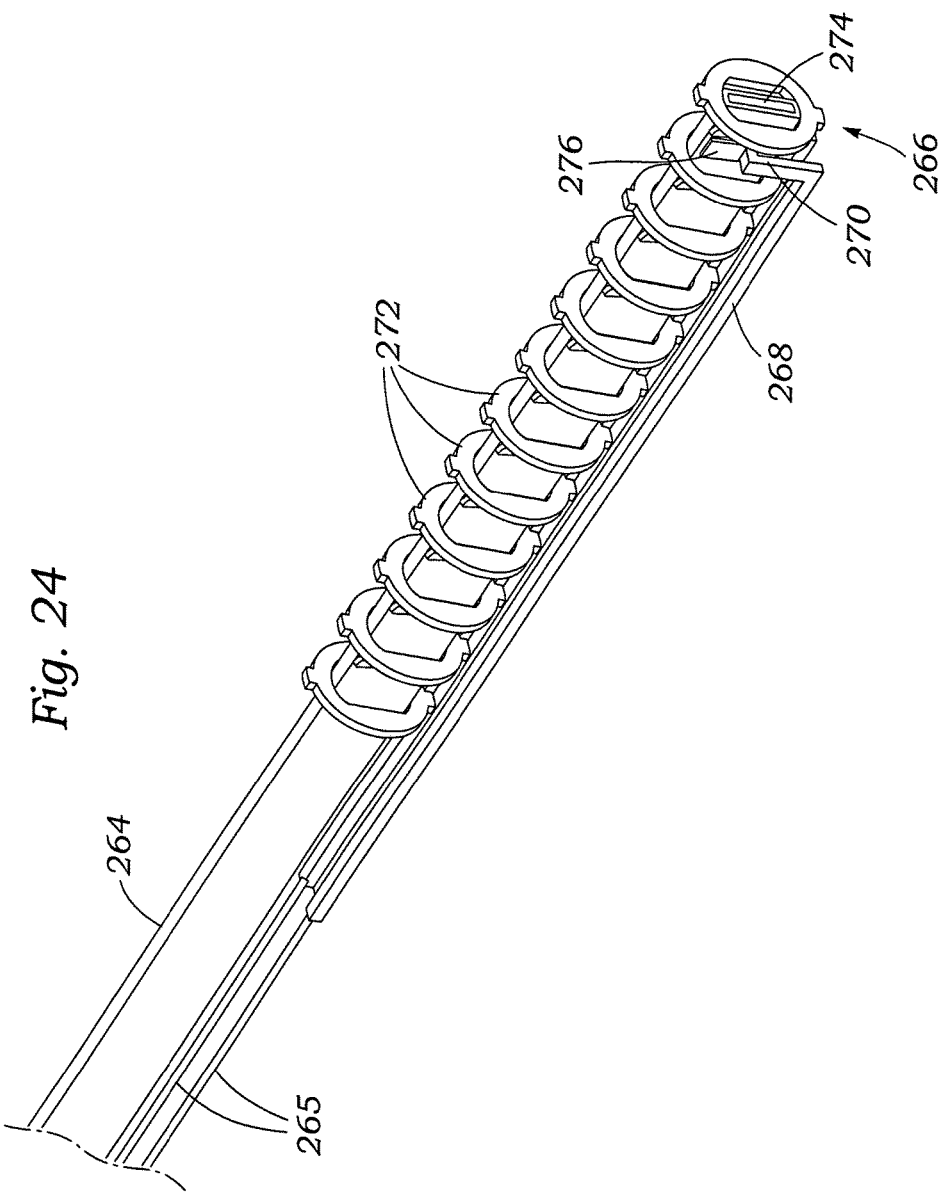
FIG. 24 shows an electric heating element at the distal end of the shaft of the device of FIG. 23.

As shown in FIGS. 23 and 24, the device 200 can include an electrical heating element 268 at the distal end of the shaft that includes a heater tip 270 located adjacent to and/or passing through a lateral opening 276 in the mandrel 264. The heater tip 270 is sufficiently close to the sutures that pass through the distal opening 274 in the mandrel and pass through the axial length of the inner lumen of the mandrel. The heating element 268 is electrically coupled via wires 256 to a heater switch 252 located in the handle portion 202 and a battery 254 located in the handle portion and/or an external power source. The heater switch 252 can be activated when the actuator 250 is depressed and can provide power from the battery 254 to the heating element 268. When activated, the heater tip 270 rapidly heats up and cuts (e.g., melts, burns, etc.) the sutures just behind the distal-most suture clip 272 that is deployed onto the sutures. The heater tip 270 can heat up in about one second in some examples, and can also cool down in about one second after the power to the heating element is ceased. This method of cutting the sutures can provide a clean end of the cut sutures without frayed fibers, which can occur after a blade-type cut of a suture. The heat can melt or fuse the suture fibers together at the free end.

In alternative embodiments of the devices disclosed herein, a suture clip can be deployed onto sutures without cutting the sutures immediately thereafter. After a suture clip is deployed onto the sutures, the device can be retracted proximally over the free ends of the sutures to allow a user to inspect the clip deployment location to verify a clip was deployed and check the accuracy and viability of the deployment clip. If the clip deployment is undesirable, the clip can be removed and a new clip can be deployed to the sutures before they are cut. The deployed clip can also be adjusted and/or the suture tension can be adjusted before cutting off the free ends of the sutures. If the clip deployment is sufficient, the device can be moved back distally over the sutures to adjacent the deployed clip, and the device can be further used to cut off the free ends of the sutures. In such embodiments, the device can include a double actuation mechanism to independently deploy the clip and re-cock the device with one user motion, and then cut the sutures with another user motion. Alternatively, another device can be used to cut the sutures after the deployment device has been removed.

In some embodiments, a vacuum system can be used to draw free ends sutures into the lumen of the mandrel. A vacuum source can be provided external to the device, or an internal vacuum source can be provided, such as within the handle portion. A hose or other conduit can couple the vacuum source to the shaft portion in order to draw air proximally through the shaft portion and create a low pressure region within the shaft that draws free ends of sutures in. In some embodiments, the shaft portion can include an adjustable door that covers and uncovers a lateral opening passing through the outer shaft, retainer and mandrel. When the door is closed, low pressure can be created inside the mandrel to draw in sutures. When the door is opened, the sutured can be grasped and pulled out laterally through the door. In other embodiments, the vacuum can be used to draw sutures all the way through the mandrel into the handle portion and/or out through a proximal opening in the handle portion. A suture clip deployment device can be configured to activate the vacuum source when the actuator is depressed, or can include a separate control for the vacuum source. Using a vacuum system to draw in sutures can eliminate the need for a snare, or can be used in conjunction with a snare.

In some embodiments, the device can comprise a vacuum monitoring system that determines and displays the pressure/vacuum level in the shaft portion and/or the amount or status of vacuum being generated or applied from a vacuum source. In some embodiments, an indicator on a display, such as the display 210, can indicate whether or not the vacuum is being applied, while in other embodiments, a level of vacuum or pressure can be displayed.

In some embodiments, the device can comprise a suture clip monitoring system that tracks/determines and displays the number of clips remaining loaded in the device. The device can comprise a display, such as the rear display 210, that shows how many clips remain. In some embodiments, when the last clip has been deployed, the clip monitoring system can cause the device to become locked such that actuator cannot be pulled. In some embodiments, the clip monitoring system can also display a lock-out indicator on the display. The display can be mechanical or electronic, analog or digital.

In some embodiments, the devices disclosed herein can be disposable after being used during a surgery and/or when all the loaded clips have been deployed. In other embodiments, the device can be cleaned and/or reloaded with clips and reused.

In some embodiments, the device can be reloaded with additional suture clips by removing the empty mandrel, or just the distal portion of the mandrel, and replacing it with a new mandrel or mandrel portion that is loaded with additional suture clips. For example, the mandrel can comprise a distal piece and a proximal piece that readily disconnect and reconnect. The distal piece can be removed and replaced with a new distal piece loaded with additional suture clips. In other embodiments, the mandrel and the retainer (or distal parts thereof) can be replaced together. In other embodiments, the entire shaft portion (of a distal part thereof) can be replaced to reload the device. In still other embodiments, additional suture clips can be placed onto the existing mandrel to reload the device.

In some embodiments, any of the devices disclosed herein can include a visual monitoring system configured to capture visual information from or near the distal end of the shaft and transfer the captured visual information to a proximal visual display. For example, the device can include a camera or endoscope positioned near the distal end of the outer shaft that is coupled via wiring to an adaptor extending from the handle and configured to be coupled to an external monitor that a user can view to assist in the clip deployment process.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

In view of the many possible embodiments to which the principles of the disclosure may be applied, it should be recognized that the illustrated embodiments are only preferred examples and should not be taken as limiting the scope of the disclosure. Rather, the scope of the disclosure is at least as broad as the following claims. We therefore claim all that comes within the scope of the following claims.

The invention claimed is:

1. A device for successively deploying a plurality of preloaded suture clips onto sutures, comprising:
   a proximal handle portion comprising an actuation mechanism;
   a mandrel having an inner lumen for receiving sutures, a proximal end portion coupled to the actuation mechanism, and a distal end portion having a distal opening in communication with the inner lumen, wherein the mandrel defines an axial dimension extending between the distal end portion and the proximal end portion, and a radial dimension perpendicular to the axial dimension, and wherein the mandrel is configured to receive at least one suture extending through the distal opening and into the inner lumen; and
   a plurality of annular suture clips mounted around the distal end portion of the mandrel, the annular suture clips being generally disk shaped and having a diameter oriented in the radial dimension and a thickness oriented in the axial dimension, wherein the thickness is smaller than the diameter;
   wherein the actuation mechanism causes the mandrel to move proximally relative to the suture clips, such that a distal-most one of the suture clips slides off of a distal end of the mandrel and onto one or more sutures extending into the distal opening of the mandrel; and
   wherein, after the distal-most one of the suture clips is deployed onto one or more sutures, the actuation mechanism causes the mandrel and a remaining portion of the suture clips to move distally relative to the handle portion such that a distal-most one of the remaining portion of the suture clips is ready to be successively deployed;
   the device further comprising a retainer positioned at least partially around the mandrel and coupled to the actuation mechanism independently of the mandrel, the retainer configured to restrict the suture clips from moving proximally relative to the handle portion when the mandrel moves proximally relative to the handle portion;
   wherein the retainer comprises at least one axially extending slot that includes a plurality of circumferentially extending notches.

2. The device of claim 1, wherein the disk shaped suture clips comprise an annular outer body, one or more resiliently deformable flaps that project radially inwardly from the annular outer body and define a suture engagement aperture for frictionally engaging one or more sutures, and one or more tabs projecting radially outwardly from the annular outer body.

3. The device of claim 2, wherein the suture clips are comprised of a shape-memory material and wherein the one or more resiliently deformable flaps are held in a resiliently deformed configuration when loaded onto the mandrel, the flaps extending axially toward the handle portion along a side of the mandrel when in the resiliently deformed configuration, and wherein the flaps resiliently return toward a natural configuration projecting radially inwardly when deployed onto a suture, such that the suture clip has a flat, disk shape when deployed onto a suture.

4. The device of claim 1, wherein the actuation mechanism causes the retainer to rotate relative to the mandrel and the suture clips, and wherein the rotation of the retainer causes cutting of the one or more sutures.

5. The device of claim 1, wherein the actuation mechanism causes the retainer to rotate relative to the mandrel and the suture clips, and wherein the rotation of the retainer allows the suture clips to move distally along with the mandrel relative to the handle portion.

6. The device of claim 1, wherein the suture clips each comprise at least one radially extending tab that projects into the axially extending slot in the retainer and is positioned in one of the circumferentially extending notches.

7. The device of claim 6, wherein the retainer has a first rotational position wherein the at least one tab of each suture clips is positioned in a respective one of the notches such that axial motion of the suture clips relative to the retainer is restricted, and wherein the retainer has a second rotational position wherein the at least one tab of each suture clip is not positioned in one of the notches and the suture clips are allowed to move axially relative to the retainer.

8. The device of claim 1, further comprising an electrical heating element positioned at a distal end of the mandrel, the heating element configured to cut a suture after a suture clip is deployed onto the suture.

9. A device for successively deploying a plurality of preloaded suture clips onto sutures, comprising:
- a proximal handle portion comprising an actuation mechanism;
- a mandrel having an inner lumen for receiving sutures, a proximal end portion coupled to the actuation mechanism, and a distal end portion having a distal opening in communication with the inner lumen, wherein the mandrel defines an axial dimension extending between the distal end portion and the proximal end portion, and a radial dimension perpendicular to the axial dimension, and wherein the mandrel is configured to receive at least one suture extending through the distal opening and into the inner lumen; and
- a plurality of annular suture clips mounted around the distal end portion of the mandrel, the annular suture clips being generally disk shaped and having a diameter oriented in the radial dimension and a thickness oriented in the axial dimension, wherein the thickness is smaller than the diameter;
- wherein the actuation mechanism causes the mandrel to move proximally relative to the suture clips, such that a distal-most one of the suture clips slides off of a distal end of the mandrel and onto one or more sutures extending into the distal opening of the mandrel; and
- wherein, after the distal-most one of the suture clips is deployed onto one or more sutures, the actuation mechanism causes the mandrel and a remaining portion of the suture clips to move distally relative to the handle portion such that a distal-most one of the remaining portion of the suture clips is ready to be successively deployed;
- the device further comprising a retainer positioned at least partially around the mandrel and coupled to the actuation mechanism independently of the mandrel, the retainer configured to restrict the suture clips from moving proximally relative to the handle portion when the mandrel moves proximally relative to the handle portion;
- wherein the actuation mechanism causes the retainer to rotate relative to the mandrel and the suture clips, and wherein the rotation of the retainer allows the suture clips to move distally along with the mandrel relative to the handle portion.

10. The device of claim 9, wherein the disk shaped suture clips comprise an annular outer body, one or more resiliently deformable flaps that project radially inwardly from the annular outer body and define a suture engagement aperture for frictionally engaging one or more sutures, and one or more tabs projecting radially outwardly from the annular outer body.

11. The device of claim 10, wherein the retainer is simultaneously engaged with the one or more tabs of each of the plurality of annular suture clips mounted around the distal end portion of the mandrel.

12. The device of claim 10, wherein the suture clips are comprised of a shape-memory material and wherein the one or more resiliently deformable flaps are held in a resiliently deformed configuration when loaded onto the mandrel, the flaps extending axially toward the handle portion along a side of the mandrel when in the resiliently deformed configuration, and wherein the flaps resiliently return toward a natural configuration projecting radially inwardly when deployed onto a suture, such that the suture clip has a flat, disk shape when deployed onto a suture.

13. A device for successively deploying a plurality of preloaded suture clips onto sutures, comprising:
- a proximal handle portion comprising an actuation mechanism;
- a mandrel having an inner lumen for receiving sutures, a proximal end portion coupled to the actuation mechanism, and a distal end portion having a distal opening in communication with the inner lumen, wherein the mandrel defines an axial dimension extending between the distal end portion and the proximal end portion, and a radial dimension perpendicular to the axial dimension, and wherein the mandrel is configured to receive at least one suture extending through the distal opening and into the inner lumen; and
- a plurality of annular suture clips mounted around the distal end portion of the mandrel, the annular suture clips being generally disk shaped and having a diameter oriented in the radial dimension and a thickness oriented in the axial dimension, wherein the thickness is smaller than the diameter;
- wherein the actuation mechanism causes the mandrel to move proximally relative to the suture clips, such that a distal-most one of the suture clips slides off of a distal end of the mandrel and onto one or more sutures extending into the distal opening of the mandrel; and
- wherein, after the distal-most one of the suture clips is deployed onto one or more sutures, the actuation mechanism causes the mandrel and a remaining portion of the suture clips to move distally relative to the handle portion such that a distal-most one of the remaining portion of the suture clips is ready to be successively deployed;
- the device further comprising a retainer positioned at least partially around the mandrel and coupled to the actuation mechanism independently of the mandrel, the retainer configured to restrict the suture clips from moving proximally relative to the handle portion when the mandrel moves proximally relative to the handle portion;
- wherein the retainer is simultaneously engaged with each of the plurality of suture clips mounted around the distal end portion of the mandrel.

14. The device of claim 13, wherein each of the plurality of suture clips comprise an annular outer body, one or more resiliently deformable flaps that project radially inwardly from the annular outer body and define a suture engagement aperture for frictionally engaging one or more sutures, and one or more tabs projecting radially outwardly from the annular outer body;
- wherein the retainer is simultaneously engaged with the one or more tabs of each of the plurality of suture clips.

15. The device of claim 14, wherein the retainer comprises a plurality of notches that engage with the one or more tabs of each of the plurality of suture clips.

16. The device of claim 14, wherein the retainer comprises an axially extending slot that allows the one or more tabs of each of the plurality of suture clips to move distally along the slot relative to the retainer.

* * * * *